United States Patent
Libbus et al.

(10) Patent No.: US 9,919,157 B2
(45) Date of Patent: Mar. 20, 2018

(54) IMPLANTABLE NEUROSTIMULATOR-IMPLEMENTED METHOD FOR MANAGING BRADYCARDIA THROUGH VAGUS NERVE STIMULATION

(71) Applicant: CYBERONICS, INC., Houston, TX (US)

(72) Inventors: Imad Libbus, St. Paul, MN (US);
Badri Amurthur, Los Gatos, CA (US);
Bruce H. KenKnight, Maple Grove, MN (US)

(73) Assignee: Cyberonics, Inc., Houston, TX (US)

( * ) Notice: Subject to any disclaimer, the term of this patent is extended or adjusted under 35 U.S.C. 154(b) by 606 days.

(21) Appl. No.: 14/177,542

(22) Filed: Feb. 11, 2014

(65) Prior Publication Data

US 2014/0155949 A1  Jun. 5, 2014

Related U.S. Application Data

(63) Continuation of application No. 13/554,656, filed on Jul. 20, 2012, now Pat. No. 8,688,212.

(51) Int. Cl.
*A61N 1/365* (2006.01)
*A61B 5/0464* (2006.01)
*A61N 1/36* (2006.01)

(52) U.S. Cl.
CPC ............ *A61N 1/365* (2013.01); *A61B 5/0464* (2013.01); *A61N 1/36114* (2013.01);
(Continued)

(58) Field of Classification Search
CPC ............ A61N 1/36139; A61N 1/36053; A61N 1/36114; A61N 1/36135; A61N 1/05; A61N 1/36175; A61N 1/365; A61N 1/36
(Continued)

(56) References Cited

U.S. PATENT DOCUMENTS 5,522,854 A   6/1996  Idecker et al.
5,707,400 A   1/1998  Terry, Jr. et al.
(Continued)

FOREIGN PATENT DOCUMENTS

WO   WO199321824   11/1993
WO   2003018113    3/2003
(Continued)

OTHER PUBLICATIONS

US 8,315,702, 11/2012, Chavan et al. (withdrawn)
(Continued)

*Primary Examiner* — Niketa Patel
*Assistant Examiner* — Minh Duc Pham
(74) *Attorney, Agent, or Firm* — Foley & Lardner LLP

(57) ABSTRACT

A method for managing bradycardia through vagus nerve stimulation is provided. An implantable neurostimulator configured to deliver electrical therapeutic stimulation in both afferent and efferent directions of a patient's cervical vagus nerve is provided. An operating mode is stored, which includes parametrically defining a maintenance dose of the electrical therapeutic stimulation tuned to restore cardiac autonomic balance through continuously-cycling, intermittent and periodic electrical pulses. The maintenance dose is delivered via a pulse generator through a pair of helical electrodes via an electrically coupled nerve stimulation therapy lead independent of cardiac cycle. The patient's physiology is monitored, and upon sensing a condition indicative of bradycardia, the delivery of the maintenance dose is suspended. A progressively increasing amount of time is spent waiting via a controller and, upon sensing a condition indicative of an absence or termination of the bradycardia, a progressively increasing partial maintenance dose is delivered via the pulse generator.

15 Claims, 6 Drawing Sheets

(52) U.S. Cl.
CPC ..... *A61N 1/36139* (2013.01); *A61N 1/36167* (2013.01); *A61N 1/36175* (2013.01); *A61N 1/36171* (2013.01)

(58) Field of Classification Search
USPC .......................................................... 607/17
See application file for complete search history.

(56) References Cited

U.S. PATENT DOCUMENTS

| | | |
|---|---|---|
| 5,928,272 A | 7/1999 | Adkins et al. |
| 5,978,709 A | 11/1999 | Begemann et al. |
| 6,006,134 A | 12/1999 | Hill et al. |
| 6,266,564 B1 | 7/2001 | Hill et al. |
| 6,354,991 B1 | 3/2002 | Gross et al. |
| 6,449,507 B1 | 9/2002 | Hill et al. |
| 6,473,644 B1 | 10/2002 | Terry et al. |
| 6,508,771 B1 | 1/2003 | Padmanabhan et al. |
| 6,522,926 B1 | 2/2003 | Kieval et al. |
| 6,600,954 B2 | 7/2003 | Cohen et al. |
| 6,610,713 B2 | 8/2003 | Tracey |
| 6,616,624 B1 | 9/2003 | Kieval |
| 6,622,041 B2 | 9/2003 | Terry, Jr. et al. |
| 6,652,449 B1 | 11/2003 | Gross et al. |
| 6,684,105 B2 | 1/2004 | Cohen et al. |
| 6,690,971 B2 | 2/2004 | Schauerte et al. |
| 6,712,772 B2 | 3/2004 | Cohen et al. |
| 6,718,208 B2 | 4/2004 | Hill et al. |
| 6,838,471 B2 | 1/2005 | Tracey |
| 6,839,594 B2 | 1/2005 | Cohen et al. |
| 6,850,801 B2 | 2/2005 | Kieval et al. |
| 6,862,480 B2 | 3/2005 | Cohen et al. |
| 6,892,098 B2 | 5/2005 | Ayal et al. |
| 6,896,651 B2 | 5/2005 | Gross et al. |
| 6,904,318 B2 | 6/2005 | Hill et al. |
| 6,907,295 B2 | 6/2005 | Gross et al. |
| 6,963,773 B2 | 11/2005 | Borschowa et al. |
| 6,963,779 B1 | 11/2005 | Shankar |
| 6,985,774 B2 | 1/2006 | Kieval et al. |
| 7,010,345 B2 | 3/2006 | Hill et al. |
| 7,072,720 B2 | 7/2006 | Puskas |
| 7,123,961 B1 | 10/2006 | Kroll et al. |
| 7,136,705 B1 | 11/2006 | Park |
| 7,139,607 B1 | 11/2006 | Shelchuk |
| 7,158,832 B2 | 1/2007 | Kieval et al. |
| 7,184,828 B2 | 2/2007 | Hill et al. |
| 7,184,829 B2 | 2/2007 | Hill et al. |
| 7,189,204 B2 | 3/2007 | Ni et al. |
| 7,218,964 B2 | 5/2007 | Hill et al. |
| 7,221,979 B2 | 5/2007 | Zhou et al. |
| 7,225,017 B1 | 5/2007 | Shelchuk |
| 7,225,019 B2 | 5/2007 | Jahns et al. |
| 7,237,320 B2 | 7/2007 | Lam |
| 7,245,967 B1 | 7/2007 | Shelchuk |
| 7,260,431 B2 | 8/2007 | Libbus et al. |
| 7,269,457 B2 | 9/2007 | Shafer et al. |
| 7,277,761 B2 | 10/2007 | Shelchuk |
| 7,295,881 B2 | 11/2007 | Cohen et al. |
| 7,305,265 B2 | 12/2007 | Fukui |
| 7,321,793 B2 | 1/2008 | Ben-Ezra et al. |
| 7,324,853 B2 | 1/2008 | Ayal et al. |
| 7,336,997 B2 | 2/2008 | Fukui |
| 7,346,398 B2 | 3/2008 | Gross et al. |
| 7,387,603 B2 | 6/2008 | Gross et al. |
| 7,389,149 B2 | 6/2008 | Rossing et al. |
| 7,395,119 B2 | 7/2008 | Hagen et al. |
| 7,403,819 B1 | 7/2008 | Shelchuck et al. |
| 7,418,292 B2 | 8/2008 | Shafer |
| 7,452,800 B2 | 11/2008 | Sosnowchik et al. |
| 7,480,532 B2 | 1/2009 | Kieval et al. |
| 7,481,759 B2 | 1/2009 | Whitehurst et al. |
| 7,485,104 B2 | 2/2009 | Kieval |
| 7,493,167 B2 | 2/2009 | Hussein et al. |
| 7,499,742 B2 | 3/2009 | Bolea et al. |
| 7,499,747 B2 | 3/2009 | Kieval et al. |
| 7,499,748 B2 | 3/2009 | Moffit et al. |
| 7,502,650 B2 | 3/2009 | Kieval |
| 7,542,800 B2 | 6/2009 | Libbus et al. |
| 7,548,780 B2 | 6/2009 | Libbus et al. |
| 7,551,958 B2 | 6/2009 | Libbus et al. |
| 7,561,922 B2 | 7/2009 | Cohen et al. |
| 7,561,923 B2 | 7/2009 | Libbus et al. |
| 7,570,999 B2 | 8/2009 | Libbus et al. |
| 7,582,053 B2 | 9/2009 | Gross et al. |
| 7,584,004 B2 | 9/2009 | Caparso et al. |
| 7,587,238 B2 | 9/2009 | Moffitt et al. |
| 7,606,622 B2 | 10/2009 | Reeve |
| 7,613,511 B2 | 11/2009 | Wu et al. |
| 7,613,516 B2 | 11/2009 | Cohen et al. |
| 7,616,990 B2 | 11/2009 | Chavan et al. |
| 7,617,003 B2 | 11/2009 | Caparso et al. |
| 7,623,926 B2 | 11/2009 | Rossing et al. |
| 7,627,384 B2 | 12/2009 | Ayal et al. |
| 7,628,750 B2 | 12/2009 | Cohen et al. |
| 7,630,760 B2 | 12/2009 | Libbus et al. |
| 7,634,315 B2 | 12/2009 | Cholette |
| 7,634,317 B2 | 12/2009 | Ben-David et al. |
| 7,640,057 B2 | 12/2009 | Libbus et al. |
| 7,647,101 B2 | 1/2010 | Libbus et al. |
| 7,647,114 B2 | 1/2010 | Libbus |
| 7,650,190 B2 | 1/2010 | Zhou et al. |
| 7,657,312 B2 | 2/2010 | Pastore |
| 7,660,628 B2 | 2/2010 | Libbus et al. |
| 7,664,548 B2 | 2/2010 | Amurthur et al. |
| 7,668,602 B2 | 2/2010 | Ben-David et al. |
| 7,672,633 B2 | 3/2010 | Zhou et al. |
| 7,676,275 B1 | 3/2010 | Farazi et al. |
| 7,689,286 B2 | 3/2010 | Pastore et al. |
| 7,711,415 B1 | 5/2010 | Farazi et al. |
| 7,711,421 B2 | 5/2010 | Shafer et al. |
| 7,734,355 B2 | 6/2010 | Cohen et al. |
| 7,751,884 B2 | 7/2010 | Ternes et al. |
| 7,769,442 B2 | 8/2010 | Shafer |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,783,353 B2 | 8/2010 | Libbus et al. |
| 7,797,041 B2 | 9/2010 | Libbus et al. |
| 7,801,603 B2 | 9/2010 | Westlund et al. |
| 7,801,604 B2 | 9/2010 | Brockway et al. |
| 7,801,614 B2 | 9/2010 | Rossing et al. |
| 7,805,193 B2 | 9/2010 | Libbus et al. |
| 7,805,203 B2 | 9/2010 | Ben-David |
| 7,813,805 B1 | 10/2010 | Farazi |
| 7,813,812 B2 | 10/2010 | Kieval et al. |
| 7,835,797 B2 | 11/2010 | Rossing et al. |
| 7,840,266 B2 | 11/2010 | Libbus et al. |
| 7,840,271 B2 | 11/2010 | Kieval et al. |
| 7,844,346 B2 | 11/2010 | Cohen et al. |
| 7,848,812 B2 | 12/2010 | Crowley et al. |
| 7,848,816 B1 | 12/2010 | Wenzel et al. |
| 7,869,869 B1 | 2/2011 | Farazi |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,894,907 B2 | 2/2011 | Cowan et al. |
| 7,904,151 B2 | 3/2011 | Ben-David |
| 7,904,175 B2 | 3/2011 | Scott et al. |
| 7,904,176 B2 | 3/2011 | Ben-Ezra et al. |
| 7,908,008 B2 | 3/2011 | Ben-David et al. |
| 7,916,013 B2 | 3/2011 | Stevenson |
| 7,925,342 B2 | 4/2011 | Badri et al. |
| 7,925,352 B2 | 4/2011 | Stack et al. |
| 7,974,693 B2 | 7/2011 | Ben-David et al. |
| 8,005,542 B2 | 8/2011 | Ben-Ezra et al. |
| 8,005,545 B2 | 8/2011 | Ben-David et al. |
| 8,036,745 B2 | 10/2011 | Ben-David et al. |
| 8,060,197 B2 | 11/2011 | Ben-David et al. |
| 8,065,021 B2 | 11/2011 | Gross et al. |
| 8,083,663 B2 | 12/2011 | Gross et al. |
| 8,116,881 B2 | 2/2012 | Cohen et al. |
| 8,131,362 B2 | 3/2012 | Moffitt et al. |
| 8,160,701 B2 | 4/2012 | Zhao et al. |
| 8,160,705 B2 | 4/2012 | Stevenson et al. |

(56) References Cited

U.S. PATENT DOCUMENTS

| | | |
|---|---|---|
| 8,195,290 B2 | 6/2012 | Brockway |
| 8,224,436 B2 | 7/2012 | Libbus et al. |
| 8,249,711 B2 | 8/2012 | Libbus et al. |
| 8,369,943 B2 | 2/2013 | Shuros et al. |
| 8,386,038 B2 | 2/2013 | Bianchi et al. |
| 8,401,640 B2 | 3/2013 | Zhao et al. |
| 8,417,354 B2 | 4/2013 | Zhang et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,634,921 B2 | 1/2014 | Chavan et al. |
| 8,688,212 B2 | 4/2014 | Libbus et al. |
| 2002/0107553 A1 | 8/2002 | Hill et al. |
| 2003/0040774 A1 | 2/2003 | Terry et al. |
| 2003/0153954 A1 | 8/2003 | Park et al. |
| 2003/0171781 A1 | 9/2003 | Florio et al. |
| 2004/0199210 A1 | 10/2004 | Shelchuk |
| 2004/0210261 A1 | 10/2004 | King et al. |
| 2004/0215265 A1 | 10/2004 | Keizer |
| 2005/0049655 A1 | 3/2005 | Boveja et al. |
| 2005/0065553 A1 | 3/2005 | Ben-Ezra et al. |
| 2005/0125044 A1 | 6/2005 | Tracey |
| 2005/0131467 A1 | 6/2005 | Boveja |
| 2005/0165465 A1 | 7/2005 | Pianca et al. |
| 2005/0267542 A1 | 12/2005 | David et al. |
| 2006/0100668 A1 | 5/2006 | Ben-David et al. |
| 2006/0190053 A1 | 8/2006 | Dobak, III |
| 2006/0206155 A1 | 9/2006 | Ben-David et al. |
| 2006/0253161 A1 | 11/2006 | Libbus et al. |
| 2007/0067004 A1 | 3/2007 | Boveja et al. |
| 2007/0093870 A1 | 4/2007 | Maschino et al. |
| 2007/0179543 A1 | 8/2007 | Ben-David et al. |
| 2007/0213773 A1 | 9/2007 | Hill et al. |
| 2007/0233194 A1 | 10/2007 | Craig |
| 2007/0255320 A1 | 11/2007 | Inman et al. |
| 2007/0276453 A1 | 11/2007 | Hill et al. |
| 2008/0015659 A1 | 1/2008 | Zhang et al. |
| 2008/0021503 A1 | 1/2008 | Whitehurst et al. |
| 2008/0033511 A1 | 2/2008 | Dobak |
| 2008/0051839 A1 | 2/2008 | Libbus et al. |
| 2008/0058874 A1 | 3/2008 | Westlund et al. |
| 2008/0061240 A1 | 3/2008 | Heuft |
| 2008/0091240 A1 | 4/2008 | Ben-David et al. |
| 2008/0132983 A1 | 6/2008 | Cohen et al. |
| 2008/0147140 A1 | 6/2008 | Ternes et al. |
| 2008/0183258 A1 | 7/2008 | Inman |
| 2008/0243196 A1 | 10/2008 | Libbus et al. |
| 2008/0319513 A1 | 12/2008 | Pu et al. |
| 2009/0030493 A1 | 1/2009 | Colburn et al. |
| 2009/0118777 A1 | 5/2009 | Iki et al. |
| 2009/0124848 A1 | 5/2009 | Miazga |
| 2009/0149900 A1 | 6/2009 | Moffitt et al. |
| 2009/0248097 A1 | 10/2009 | Tracey et al. |
| 2009/0270953 A1 | 10/2009 | Ecker et al. |
| 2009/0275956 A1 | 11/2009 | Burnes et al. |
| 2010/0010556 A1 | 1/2010 | Zhao et al. |
| 2010/0010603 A1 | 1/2010 | Ben-David et al. |
| 2010/0016919 A1 | 1/2010 | Hill et al. |
| 2010/0042173 A1 | 2/2010 | Farazi et al. |
| 2010/0114197 A1 | 5/2010 | Burnes et al. |
| 2010/0114203 A1 | 5/2010 | Burnes et al. |
| 2010/0114227 A1 | 5/2010 | Cholette |
| 2010/0174341 A1 | 7/2010 | Bolea et al. |
| 2010/0286740 A1 | 11/2010 | Libbus et al. |
| 2010/0331908 A1 | 12/2010 | Farazi |
| 2011/0015692 A1 | 1/2011 | Libbus et al. |
| 2011/0082514 A1 | 4/2011 | Libbus et al. |
| 2011/0098796 A1 | 4/2011 | Ben-David et al. |
| 2011/0224749 A1 | 9/2011 | Ben-David et al. |
| 2011/0257708 A1 | 10/2011 | Kramer et al. |
| 2012/0143286 A1 | 6/2012 | Hahn et al. |
| 2012/0172742 A1 | 7/2012 | Arcot-Krishnamurthy et al. |
| 2012/0185007 A1 | 7/2012 | Ziegler et al. |
| 2012/0185010 A1 | 7/2012 | Zhou et al. |
| 2012/0192874 A1 | 8/2012 | Bolea et al. |
| 2012/0271374 A1 | 10/2012 | Nelson et al. |
| 2012/0303080 A1* | 11/2012 | Ben-David .......... A61N 1/0556 607/14 |
| 2012/0330373 A1* | 12/2012 | Ternes ............... A61N 1/36053 607/42 |
| 2013/0158616 A1 | 6/2013 | Libbus et al. |
| 2013/0158617 A1 | 6/2013 | Libbus et al. |
| 2013/0158618 A1 | 6/2013 | Libbus et al. |
| 2013/0238047 A1 | 9/2013 | Libbus et al. |
| 2013/0289646 A1 | 10/2013 | Libbus et al. |
| 2014/0135862 A1 | 5/2014 | Libbus et al. |
| 2014/0135863 A1 | 5/2014 | Libbus et al. |
| 2014/0135864 A1 | 5/2014 | Libbus et al. |
| 2014/0228905 A1 | 8/2014 | Bolea |
| 2014/0277232 A1 | 9/2014 | Libbus et al. |
| 2015/0073511 A1 | 3/2015 | Libbus et al. |
| 2015/0073512 A1 | 3/2015 | Libbus et al. |
| 2015/0094962 A1 | 4/2015 | Hoegh et al. |
| 2015/0119956 A1 | 4/2015 | Libbus et al. |
| 2015/0119959 A1 | 4/2015 | Libbus et al. |
| 2015/0196762 A1 | 7/2015 | Amurthur et al. |

FOREIGN PATENT DOCUMENTS

| | | |
|---|---|---|
| WO | 2003099373 | 12/2003 |
| WO | 2003099377 | 12/2003 |
| WO | 2004110549 | 12/2004 |
| WO | 2004110550 | 12/2004 |
| WO | 2005011805 | 2/2005 |
| WO | 2006019764 | 2/2006 |
| WO | WO2010005482 A1 | 1/2010 |

OTHER PUBLICATIONS

PCT Application No. PCT/US2013/050390, International Preliminary Report on Patentability dated Oct. 14, 2014, 14 pages.

PCT Application No. PCT/US2014/024827, Search Report and Written Opinion dated Nov. 11, 2014, 18 pages.

PCT Application No. PCT/US2012/068205, Search Report and Written Opinion dated Feb. 8, 2013, 15 pages.

PCT Application No. PCT/US2012/068213, Search Report and Written Opinion dated Mar. 15, 2013, 11 pages.

PCT Application No. PCT/US2012/068223, Search Report and Written Opinion dated Apr. 3, 2013, 11 pages.

PCT Application No. PCT/US2013/021964, Search Report and Written Opinion dated Apr. 17, 2013, 10 pages.

PCT Application No. PCT/US2012/068211, Search Report and Written Opinion dated May 7, 2013, 9 pages.

PCT Application No. PCT/US2013/050390, Search Report and Written Opinion dated Nov. 5, 2013.

PCT Application No. PCT/US2013/068541, Search Report and Written Opinion dated Jan. 7, 2014.

Abraham, et al., "Devices in the management of advanced, chronic heart failure," Nature Reviews, vol. 10, pp. 98-110 (Feb. 2013) (Published online Dec. 11, 2012).

Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).

Agostoni, et al., "Functional and Histological Studies of the Vagus Nerve and its Branches to the Heart, Lungs and Abdominal Viscera in the Cat," J. Physiol. 135, pp. 182-205 (1957).

Ajani, et al., "Prevalence of High C-Reactive Protein in Persons with Serum Lipid Concentrations within Recommended Values," Chemical Chemistry, 50:9, pp. 1618-1622 (2004).

Akiyama, et al., "Effects of right and left vagal stimulation on left ventricular acetylcholine levels in the cat," Acta Physiol Scand, 172, pp. 11-16 (2001).

Anand, et al., "C-Reactive Protein in Heart Failure: Prognostic Value and the Effect of Valsartan," Circulation, Journal of the American Heart Association, 112, pp. 1428-1434 (2005).

Anholt, et al., "Recruitment and blocking properties of the CardioFit stimulation lead," Journal of Neural Engineering, 8, pp. 1-6, (2011).

(56) References Cited

OTHER PUBLICATIONS

Ardell, et al., "Selective vagal innervation of sinoatrial and atrioventricular nodes in canine heart," Am. J. Physiol. 251 (Heart Circ. Physiol. 20), pp. H764-H773 (1986).
Armour, "Cardiac neuronal hierarchy in health and disease," Am J Physiol Regul Integr Comp Physiol, 287, pp. R262-R271 (2004).
Armour, "Myocardial ischaemia and the cardiac nervous system," Cardiovascular Research, 41, pp. 41-54 (1999).
Armour, "The little brain on the heart," Cleveland Clinic Journal of Medicine, vol. 74, supp. 1, pp. S48-S51 (Feb. 2007).
Armour, et al., "Functional anatomy of canine cardiac nerves," Acta anat., 91, pp. 510-528 (1975).
Armour, et al., "Localized myocardial responses to stimulation of small cardiac branches of the vagus," American Journal of Physiology, vol. 228, No. 1 pp. 141-148 (Jan. 1975).
Armour, JA, "Potential clinical relevance of the 'little brain' on the mammalian heart," Experimental Physiology, vol. 1 93, No. 2, pp. 165-176 (Feb. 2008). Online Publication Date: Nov. 2, 2007. Available at: http://ep.physoc.org/ content/93/2/165.long.
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at ww.boddunan.com/education/20-medicine-a-surgery/12730-nerver-fiber-types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation,Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning a new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal is an Integral Component of Autonomic Imbalance in Congestive Heart Failure: Demonstration in Human Subjects and Verification in a Paced Canine Model of Ventricular Failure,"JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).
Borovilkova, et al., "Vagus nerve stimulation attenuates the systemic inflammatory response to endotoxin," Nature, vol. 405, pp. 458-462 (May 25, 2000).
Brack, et al., "Mechanisms underlying the autonomic modulation of ventricular fibrillation initiation—tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al., "Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Castoro et al.,"Excitation properties of the right cervical vagus nerve in adult dogs," Experimental Neurology, vol. 2 227, iss. 1, pp. 62-68 (Jan. 2011). Online Publication Date: Sep. 17, 2010. Available at: http://www.sciencedirecl.com/science/article/pii/SOO1448861000347X.
Castoro, et al., "Excitation properties of the right cervical vagus nerve in adult dogs," Experimental Neurology, 227 (pp. 62-68 (2011).
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari et al., "Chronic vagus nerve stimulation: a new and promising therapeutic approach for chronic heart failure," European Heart Journal, vol. 32, iss. 7, pp. 847-855 (Apr. 2011). Online publication date: Oct. 28, 2010. Available at: http://eurheartj.oxfordjournals.org/content/3217/84 7.long.
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Chronic vagus nerve stimulation: a new and promising therapeutic approach for chronic heart failure," European Heart Journal, 32, pp. 847-855 (2011).
De Ferrari, et al., "Vagus nerve stimulation: from pre-clinical to clinical application: challenges and future directions," Heart Fail Rev, 16, pp. 195-203 (2011).

(56) References Cited

OTHER PUBLICATIONS

De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).
Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).
Dunlap, et al., "Mechanisms of altered vagal control in heart failure: influence of muscarinic receptors and acetylcholinesterase activity," Am J Physiol Heart Circ Physiol, 285, pp. H1632-H1640 (Jun. 26, 2003).
Elsenbruch, et al., "Heart Rate Variability During Waking and Sleep in Healthy Males and Females," Sleep, vol. 22, No. 8, pp. 1067-1071 (1999).
Euler, et al., "Acetylcholine release by a stimulus train lowers atrial fibrillation threshold," Am. J Physiol. 253 (Heart Circ. Physiol, 22), pp. H863-H868 (1987).
Evans, et al., "Histological and functional studies on the fibre composition of the vagus nerve of the rabbit," Journal of Anatomy, 130, pp. 139-151 (1954).
Fallen, "Vagal Afferent Stimulation as a Cardioprotective Strategy? Introducing the Concept," A.N.E., vol. 10, No. 4 (Oct. 2005).
Fan, et al., "Transvenous vagus nerve stimulation: A potential heart failure therapy is feasible in humans," JACC, vol. 55, issue 10A, pp. E152-E153 (2010).
Fazan, et al., "Diabetic Peripheral Neuropathies: A Morphometric Overview," Int. J. Morphol, 28(I), pp. 51-64 (2010).
Feinauer, et al., "Ouabain enhances release of acetylcholine in the heart evoked by unilateral vagal stimulation," Arch Pharmacol, 333, pp. 7-12 (1986).
Fonarow, et al., "Incremental Reduction in Risk of Death Associated with Use of Gudeline-Recommended Therapies in Patients with Heart Failure: A Nested Case-Control Analysis of Improve HF," J Am Heart Assoc, 1, pp. 16-26 (2012).
Ford, et al., "The effects of electrical stimulation of myelinated and non-myelinated vagal fibres on heart rate in the rabbit," J. Physiol. 380, pp. 341-347 (1986).
Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).
Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).
Gatti, et al., "Can neurons in the nucleus ambiguus selectively regulate cardiac rate and atrio-ventricular conduction?" Journal of the Autonomic Nervous System, 57, pp. 123-127 (1996).
Gatti, et al., "Vagal control of left ventricular contractility is selectively mediated by a cranioventricular intracardiac ganglion in the cat," Journal of the Autonomic Nervous System, 66, pp. 138-144 (1997).
Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).
Gottdiener, et al., "Predictors of Congestive Heart Failure in the Elderly: The Cardiovascular Heatlh Study," Journal of the American College of Cardiology, vol. 35, No. 6, pp. 1628-1637 (2000).
Gray, et al., "Parasympathetic control of the Heart. II. A novel interganglionic intrinsic cardiac circuit mediates neural control of heart rate," J. Appl Physiol, 96, pp. 2273-2278 (2004).
Gray, et al., "Parasympathetic control of the Heart. III. Neuropeptide Y-immunoreactive nerve terminals synapse on three populations of negative chronotropic vagal preganglionic neurons," J. Appl Physiol, 96, pp. 2279-2287 (2004).
Grill, "Chapter 14—Principles of Electric Field Generation for Stimulation of the Central Nervous System," Neuromodulation, Academic Press (2009).
Guilleminault, et al., "Cyclical Variation of the Heart Rate in Sleep Apnoea Syndrome," The Lancet, pp. 126-131 (Jan. 21, 1984).
Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).
Hardwick, et al., "Remodeling of the guinea pig intrinsic cardiac plexus with chronic pressure overload," Am J Physiol Regulatory Integrative Comp Physiol, 297, pp. 859-866 (2009).
Hauptman, et al., "The vagus nerve and autonomic imbalance in heart failure: past, present, and future," Heart Fail Rev, 16, pp. 97-99 (2011).
Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).
Hoffman, et al., "Vagus Nerve Components," Anat Rec, 127, pp. 551-568 (1957).
Hu et al., "Role of sympathetic nervous system in myocardial ischemia injury: Beneficial or deleterious?" Letters to the Editor, Elsevier Ireland Ltd. (Mar. 27, 2012).
Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).
Huston, et al., "Splenectomy inactivates the cholinergic antiinflammatory pathway during lethal endotoxemia and polymicrobial sepsis," J. Exp. Med, vol. 203, No. 7 pp. 1623-1628 (Jun. 19, 2006).
Huston, et al., "Transcutaneous vagus nerve stimulation reduces serum high mobility group box 1 levels and improves survival in murine sepsis," Crit Care Med, vol. 35, No. 12, pp. 2762-2768 (2007).
Ingemansson, et al., "Autonomic modulation of the atrial cycle length by the head up tilt test: non-invasive evaluation in patients with chronic atrial fibrillation," Heart, 80, pp. 71-76.
Ito, et al., "Efferent sympathetic and vagal innervation of the canine right ventricle," Circulation, Journal of the American Heart Association, vol. 90, pp. 1469-1468 (1994).
Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).
Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).
Jammes, et al., "Afferent and efferent components of the bronchial vagal branches in cats," Journal of the Autonomic Nervous System, 5, pp. 165-176 (1982).
Janabi, et al., "Oxidized LDL—Induced NF-kB Activation and Subsequent Expression of Proinflammatory Genes are Defective in Monocyte-Derived Macrophages from CD36-Deficient Patients," Arterioscler Thromb Vasc Biol., 20:1953-1960 (2000).
Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).
Jessup, et al., "2009 Focused Update: ACCF/AHA Guidelines for the Diagnosis and Management of Heart Failure in Adults," Circulation, Journal of the American Heart Association, vol. 119, pp. 1977-2016 (2009).
Johnson, et al., "Parasympathetic control of the heart. I. An interventriculo-septal ganglion is the major source of the vagal intracardiac innervation of the ventricles," J Appl Physiol, 96, pp. 2265-2272 (2004).
Kakinuma, et al., "Cholinoceptive and cholinergic properties of cardiomyocytes involving an amplification mechanism for vagal

(56) References Cited

OTHER PUBLICATIONS efferent effects in sparsely innervated ventricular myocardium," FEBS Journal, 276, pp. 5111-5125 (2009).

Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).

Kaneko, et al., "C-Reactive Protein in Dilated Cardiomyopathy," Cardiology, 91, pp. 215-219 (1999).

Katare, et al., "Vagal nerve stimulation prevents reperfusion injury through inhibition of opening of mitochondrial permeability transition pore independent of bradycardiac effect," The Journal of Thoracic and Cardiovascular Surgery, vol. 137, No. 1, pp. 223-231 (2009).

Katz, et al., "Diseases of the heart in the Works of Hippocrates," Br Heart J, 24, pp. 257-264 (1962).

Kawada, et al., "High-frequency dominant depression of peripheral vagal control of heart rate in rats with chronic heart failure," Acta Physiol 207, 494-502 (2013).

Kawada, et al., "Vagal stimulation suppresses isschemia-induced myocardial interstitial norepinephrine release," Life Sciences, 78, pp. 882-887 (2006).

Kawashima, "The autonomic nervous system of the human heart with special reference to its origin, course, and peripheral distribution," Anat Embryol, 209, pp. 425-438 (2005).

Klein et al., "Vagus nerve stimulation: A new approach to reduce heart failure," Cardiology Journal, vol. 17, iss. 6, pp. 638-643 (2010).

Kliks, et al., "Influence of Sympathetic Tone on Ventricular Fibrillation Threshold During Experimental Coronary Occlusion," The American Journal of Cardiology, vol. 36, pp. 45-49 (Jul. 1975).

Kolman, et al., "The effect of vagus nerve stimulation upon vulnerability of the canine ventricle: role of sympathetic-parasympathetic interactions," Journal of the American Heart Association, 52, pp. 578-585 (1975).

Kong, et al., "Optimizing the Parameters of Vagus Nerve Stimulation by Uniform Design in Rats with Acute Myocardial Infarction," PLOS One, vol. 7, issue 11 (Nov. 2012).

Koopman, et al., "Pilot study of stimulation of the cholinergic anti-inflammatory pathway with an implantable vagus nerve stimulation device in patients with rheumatoid arthritis," Abstract (2012).

Kulbertus, et al., ed., "Neurocardiology," Futura Publishing Co., pp. 13 ("Anatomy of the Cardiac Efferent Innvervation"); 61-63 ("Autonomic Neural Control"); 87, 89, 92-93 ("Sympathetic-Parasympathetic Interactions"); 183, 187 ("Parasympathetic Nervous System"); 104 (1988).

La Rovere, et al., "Baroreflex Sensitivity and Heart Rate Variability in the Identification of Patients at Risk for Life-Threatening Arrhythmias: Implications for Clinical Trials," Circulation, Journal of the American Heart Association, 103, pp. 2072-2077 (2001).

La Rovere, et al., "Baroreflex sensitivity and heart-rate variability in prediction of total cardiac mortality after myocardial infarction. ATRAMI (Autonomic Tone and Reflexes After Myocardial Infarction) Investigators," Lancet, 351(9101), pp. 478-484 (Feb. 14, 1998).

Lane, et al., "Prediction and Prevention of Sudden Cardiac Death in Heart Failure," Heart, 91, pp. 674-680 (2005).

Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).

Lewis, et al., "Vagus nerve stimulation decreases left ventricular contractility in vivo in the human and pig heart," Journal of Physiology, 534, pp. 547-552 (2001).

Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003. Available at: http://circ.ahajournals.org/cgi/pmidlookup?view=long&pmid=14662714.

Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).

Li, et al., "Inflammatory cytokines and nitric oxide in heart failure and potential modulation by vagus nerve stimulation," Heart Fail Rev, 16, pp. 137-145 (2011).

Li, et al., "Low-Level Vagosympathetic Stimulation. A Paradox and Potential New Modality for the Treatment of Focal Atrial Fibrillation," Circ Arrhythm Electrophysiol, Journal of American Heart Association, 2, pp. 645-651 (2009).

Li, et al., "Restoration of vagal tone by donepezil, on top of Iosartan treatment, markedly suppresses ventricular dysfunction and improves long-term survival in chronic heart failure rats," European Heart Journal, 32 (Abstract Supplement), pp. 642 (2011).

Li, et al., "Vagal nerve Stimulation Markedly Improves Long-Term Survival After Chronic Heart Failure in Rats," Circulation, Journal of the American Heart Association, 109, pp. 120-124 (2004).

Libby, et al., "Inflammation and Atherosclerosis," Circulation, Journal of the American Heart Association, 105, pp. 1135-1143 (2002).

Liu, et al., "Differing sympathetic and vagal effects on atrial fibrillation in dogs: role of refractoriness heterogeneity,"Am. J. Physiol. 273 (Heart Circ. Physiol. 42), pp. H805-H816 (1997).

Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).

Lohmeier, et al., "Prolonged Activation of the Barorelfex Products Sustained Hypotension," Hypertension, Journal of the American Heart Association, 43, pp. 306-311 (2004).

Lu, et al., "Vagal nerve stimulation protects cardiac injury by attenuating mitochondrial dysfunction in a murine burn injury model," J. Cell. Mol. Med., vol. 17, No. 5, pp. 664-671 (2013).

Ma, et al., "Analysis of afferent, central, and efferent components of the baroreceptor reflex in mice," Am J Physiol Regulatory Integration Comp Physiol, 283, pp. 1033-1040 (2002).

Maj, et al., "P5775: Autonomic imbalance and circulating androgens and estrogens in men with systolic heart failure," European Heart Journal, 32 (Abstract Supplement), pp. 1090 (2011).

Malkin, et al., "Life-saving or life-prolonging? Interpreting trial data and survival curves for patients with congestive heart failure," The European Journal of Heart Failure, 7, pp. 143-148 (2005).

Mann, "Chapter 12—Peripheral Nerves," The Nervous System in Action, michaeldmann.net/mann12.html, (Jul. 2011).

Mann, "Inflammatory Mediators and the Failing Heart. Past, Present, and the Foreseeable Future," Circ Res., 91, pp. 988-998 (2002).

Mann, "Stress-Activated Cytokines and the Heart: From Adaptation to Maladaptation," Annu. Rev. Physiol., 65, pp. 81-101 (2003).

Martin-Portugues, et al., "Histopathologic features of the vagus nerve after electrical stimulation in swine," Histol Histopathol, 20, pp. 851-856 (2005).

Martins, et al., "Distribution of Local Repolarization Changes Produced by Efferent Vagal Stimulation in the Canine Ventricles," JACC, vol. 2, No. 6, pp. 1191-1199 (Dec. 1983).

Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).

May, et al., "P564: Long-term prediction of all-cause mortality in diabetic autonomic neuropathy: simple function tests or 24-hour heart rate variability (HRV)?" European Heart Journal, 32 (Abstract Supplement, pp. 64 (2011).

Mei,et al., "The Composition of the Vagus Nerve of the Cat," Cell Tissue Res., 209, pp. 423-431 (1980).

Merrill, et al., "Electrical stimulation of excitable tissue: design of efficacious and safe protocols," Journal of Neuroscience Methods, 141, pp. 171-198 (2005).

Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).

(56) References Cited

OTHER PUBLICATIONS

Murakawa, et al., "Effect of Cervical Vagal Nerve Stimulation on Defibrillation Energy," Jpn Heart J, 44, pp. 91-100 (Jan. 2003).
Naito, "Effects of zatebradine and propranolol on canine ischemia and reperfusion-induced arrhythmias," European Journal of Pharmacology, 388, pp. 171-176 (2000).
Nakajima, et al., "Autonomic Control of the Location and Rate of the Cardiac Pacemaker in the Sinoatrial Fat Pad of Parasympathetically Denervated Dog Hearts," Journal of Cardiovascular Electrophysiology, vol. 13, No. 9 pp. 896-901 (Sep. 2002).
Nearing, et al., "Crescendo in Depolarization and Repolarization Heterogeneity Heralds Development of Ventricular Tachycardia in Hospitalized Patients with Decompensated Heart Failure," Circulation Arrhythmia and Electrophysiology, Journal of the American Heart Association, 5, pp. 84-90 (2012).
Nihei, et al., "Decreased Vagal Control Over Heart Rate in Rats with Right-Sided Congestive Heart Failure—Downregulation of Neuronal Nitric Oxide Synthase," Circ J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).
Nolan, et al., "Prospective Study of Heart Rate Variability and Mortality in Chronic Heart Failure: Results of the United Kingdom Heart Failure Evaluation and Assessment of Risk Trial (UK-Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).
Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vasc Biol., 18, pp. 894-901 (1998).
Oliveira, et al., "Effects of vagal stimulation on induction and termination of atrial fibrillation in an in vivo rabbit heart model," Rev Port Cardiol, 29(03), pp. 375-389 (2010).
Olshansky et al., "Parasympathetic Nervous System and Heart Failure: Pathophysiology and Potential Implications for Therapy," Circulation: Journal of the American Heart Association, vol. 118, iss. 8, pp. 863-871 (Aug. 2008).
Olshansky, et al., "Parasympathetic Nervous System and Heart Failure: Pathophysiology and Potential Implications for Therapy," Circulation, Journal of the American Heart Association, 118, pp. 863-871 (2008).
Onkka, et al., "Sympathetic nerve fibers and ganglia in canine cervical vagus nerves: Localization and quantitation," Heart Rhythm, vol. 10, No. 4, pp. 585-591 (Apr. 2013).
Ordelman, et al., "Selectivity for Specific Cardiovascular Effects of Vagal Nerve Stimulation with a Multi-Contact Electrode Cuff," IEEE, pp. 1-6 (2011).
Packer, et al., "Effect of Carvedilol on Survival in Severe Chronic Heart Failure," The New England Journal of Medicine, vol. 344, No. 22, pp. 1651-1658 (May 31, 2001).
Pavlov, et al., "Central muscarinic cholinergic regulation of the systemic inflammatory response during endotoxemia," PNAS, vol. 103, No. 13, pp. 5219-5223 (Mar. 28, 2006).
Pavlov, et al., "Controlling inflammation: the cholinergic anti-inflammatory pathway," Biochemical Society Transactions, vol. 34, part 6, pp. 1037-1040 (2006).
Peckham, et al., "Chapter 18—Implantable Neural Stimulators," Neuromodulation, Academic Press (2009).
Pina, et al., "The Predictive Value of Biomarkers in Heart Failure," Medscape Education Cardiology, Available at http://www.medscape.org/viewarticle/765328 (CME Released: Jun. 15, 2012).
Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).
Poole-Wilson, "Relation of Pathophysiologic Mechanisms to Outcome in Heart Failure," JACC, vol. 22, No. 4 (supplement A), pp. 22A-29A (Oct. 1993).
Pye, et al., "Study of serum C-reactive protein concentration in cardiac failure," Br Heart J, 63, pp. 228-230 (1990).
Rademacher, et al., "P5878: Multidimensional holter-based analysis of cardiac autonomic regulation predicts early AF recurrence after electrical cardioversion," European Heart Journal, 32 (Abtsract Supplement), pp. 1116-1117 (2011).
Randall, et al., "Regional vagosympathetic control of the heart," American Journal of Physiology, vol. 227, No. 2, pp. 444-452 (1974).
Randall, et al., "Selective Vagal Innervation of the Heart," Annals of Clinical and Laboratory Science, vol. 16, No. 3, pp. 198-208 (1986).
Raymond, et al., "Elevated interleukin-6 levels in patients with asymptomatic left ventricular systolic dysfunction," American Heart Journal, vol. 141, No. 3, pp. 435-438 (Mar. 2001).
Rhee, et al., "Presentation Abstract—Effects of suprathreshold vagal stimulation on stellate ganglion nerve activity in ambulatory dogs," 33rd Annual Scientific Sessions, Heart Rhythm (2012).
Riccio, et al., "Interganglionic segregation of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality During a Median 3.4-Year Follow-up of Glycemic Treatment in the Accord Trial," Diabetes Care, vol. 33, No. 5, pp. 983-990 (May 2010).
Ridker, C-Reactive Protein: A Simple Test to Help Predict Risk of Heart Attack and Stroke, Journal of the American Heart Association, 108, pp. e81-e85 (2003).
Ridker, et al., "Comparison of C-Reactive Protein and Low-Density Lipoprotein Cholesterol Levels in the Prediction of First cardiovascular Events," New England Journal of Medicine, vol. 347, No. 20, pp. 1557-1566 (Nov. 14, 2002).
Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).
Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).
Roger, et al., "Heart Disease and Stroke Statistics-2011 Update: A Report from the American Heart Association," Circulation, Journal of the American Heart Association. Available at http://circ.ahajournals.org/content/123/4/e18 (2010).
Romanovsky, et al., "The vagus nerve in the thermoregulatory response to systemic inflammation," Am. J. Physiol., 273, pp. R407-R413 (1997).
Rossi, et al., "Epicardial ganglionated plexus stimulation decreases postoperative inflammatory response in humans," Heart Rhythm, vol. 9, No. 6, pp. 943-950 (Jun. 2012).
Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).
Rozman, et al., "Heart function influenced by selective mid-cervical left vagus nerve stimulation in a human case study," Hypertension Research, 32, pp. 1041-1043 (2009).
Rutecki, "Anatomical, Physiological and Theoretical Basis for the Antiepileptic Effect of Vagus Nerve Stimulation," Epilepsia, 31 (suppl. 2), pp. S1-S6 (1990).
Sabbah et al., "Vagus nerve stimulation in experimental heart failure," Heart Failure Reviews, vol. 16, No. 2, pp. 171-178 (Mar. 2011). Online Publication Date: Dec. 3, 2010.
Sabbah, et al., "3722: Vagus nerve stimulation improves left ventricular function in heart failure: results of a 6 month investigation

(56) References Cited

OTHER PUBLICATIONS with a cross-over design in dogs with experimental heart failure," European Heart Journal, 32 (Abstract Supplement), pp. 642 (2011).
Sabbah, et al., "Baroreflex Activation Therapy for the Treatment of Heart Failure," Presentation available at http://www.cvrx.com/wp/wp-content/uploads/2012/04/Dr.-Sabbah-Slides.pdf (2012).
Sabbah, et al., "Chronic Electrical Stimulation of the Carotid Sinus Baroreflex Improves Left Ventricular Function and Promotes Reversal of Ventricular Remodeling in Dogs with Advanced Heart Failure," Circulation Heart Failure, Journal of the American Heart Association, 4, pp. 65-70 (2011).
Sabbah, et al., "Vagus nerve stimulation in experimental heart failure," Heart Fail Rev, 16, pp. 171-178 (2011).
Samara, et al., "The Effects of Cardiac Resyhchronization Therapy on Chronotropic Incompetence in Patients Intolerant of Beta Antagonist Therapy," Journal of Cardiac Failure, vol. 17, No. 8S, pp. S-54-S55 (Aug. 2011).
Sanner, et al., "P4743: Prediction of cardiovascular risk from nocturnal pulse wave signal using the autonomic state indicator (ASI) technology," European Heart Journal, 32 (Abstract Supplement), pp. 839 (2011).
Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).
Schauerte, "Time for Change: Cardiac neurophysiology meets cardiac electrophysiology," Editorial Commentary, Heart Rhythm Society (2013).
Schiereck, et al., "AV blocking due to asynchronous vagal stimulation in rats," Am J Physiol Heart Circ Physiol, 278, pp. H67-H73 (2000).
Schocken, et al., "Prevalence and Mortality Rate of Congestive Heart Failure in the United States," JACC, vol. 20, No. 2, pp. 301-306 (Aug. 1992).
Schwartz, "Vagal Stimulation for Heart Diseases: From Animals to Men," Circulation Journal, vol. 75, pp. 20-27 (Jan. 2011).
Schwartz, "Vagal stimulation for heart failure," Current Opinion in Cardiology, 26, pp. 51-54 (2011).
Schwartz, "Vagal stimulation for the treatment of heart failure: a translational success story," Heart, vol. 98, No. 23, pp. 1687-1690 (2012).
Schwartz, et al. Vagal stimulation for heart failure: Background and first in-man study, Heart Rhythm, 6, 11 suppl., pp. S76-S81 (Nov. 2009).
Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypotehsis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).

Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, etl al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).
Shioi, et al., "Increased Expression of Interleukin-1B and Monocyte Chemotactic and Activating Factor/Monocyte Chemoattractant Protein-1 in the Hypertrophied and Failing Heart with Pressure Overload," Circ Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, *Crotalus durissus*," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).
Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan,. et al., "Inflammatory Markers and Risk of Heart Failure in Elderly Subjects Without Prior Myocardial Infarction," Circulation, Journal of the American Heart Association, 107, pp. 1486-1491 (2003).
Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," The Journal of Physiology, vol. 500, No. 23, pp. 6065-6074 (2012).
Wang, et al., "Nicotinic acetylcholine receptor 7 subunit is an essential regulator of inflammation," Nature, vol. 421, pp. 384-388 (Jan. 23, 2003).

(56) References Cited

OTHER PUBLICATIONS

Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).
Wann, et al., "Vulnerability for apoptosis in the limbic system after myocardial infarction in rats: a possible model for human postinfarct major depression," J Psychiatry Neurosci, 32(1):11-6, pp. 11-16 (2007).
Watkins, et al., "Cytokine-to-Brain Communication: A Review & Analysis of Alternative Mechanisms," Life Sciences, vol. 57, No. 11, pp. 1011-1026 (1995).
Whyte, et al., "Reactive oxygen species modulate neuronal excitability in rat intrinsic cardiac ganglia," Auton Neurosci, 150(1-2), pp. 45-52 (Oct. 5, 2009).
Wieland, et al., "Bradycardic and proarrhythmic properties of sinus node inhibitors," Abstract, Molecular Pharmacology, 69(4):1328-37 (2006).
Yang, et al., "Sustained increases in heart rate induced by time repetition of vagal stimulation in dogs," Am. J. Physiol., 249, pp. H703-H709 (1985).
Yin, et al., "Independent prognostic value of elevated high-sensitivity C-reactive protein in chronic heart failure," American Heart Journal, vol. 147, No. 5, pp. 931-938 (2004).
Yndestad, et al., "Systemic inflammation in heart failure—The whys and wherefores," Heart Fail Rev, 11, pp. 83-92 (2006).
Yoo, et al., "High-resolution measurement of electrically-evoked vagus nerve activity in the anesthetized dog," J. Neural Eng., 10, pp. 1-9 (2013).
Yoo, et al., "Selective Control of Physiological Responses by Temporally-Patterned Electrical Stimulation of the Canine Vagus Nerve," 33rd Annual International Conference of the IEEE EMBS (2011).
Yu, et al., "Interactions between atrial electrical remodeling and autonomic remodeling: How to break the vicious cycle," Heart Rhythm, 9, pp. 804-809 (2012).
Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).
Yuan, et al., "Gross and Microscopic Anatomy of the Canine Intrinsic Cardiac Nervous System," The Anatomical Record, 239, pp. 75-87 (1994).
Yusuf, et al., "Changes in Hypertension Treatment and in Congestive Heart Failure Mortality in the United States," Hypertension, Journal of the American Heart Association, 13:I74-I179 (1989).
Zhang, et al., "Arrhythimias and vagus nerve stimulation," Heart Fail Rev, 16, pp. 147-161 (2011).
Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).
Zhang, et al., "Involvement of activated astrocyte and microglia of locus coeruleus in cardiac pain processing after acute cardiac injury," Neurol Res, 31, pp. 432-438 (2009).
Zhang, et al., "Relationship between right cervical vagus nerve stimulation and atrial fibrillation inducibility: Therapeutic intensities do not increase arrhythmogenesis," Heart Rhythm, 6, pp. 244-250 (2009).
Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).
Zheng, et al., "Vagal stimulation markedly suppresses arrhythmias in conscioius rats with chronic heart failure after myocardial infarction," Proceedings of the 2005 IEEE (2005).
Zipes, et al., "Effects of selective vagal and stellate ganglion stimulation on atrial refractoriness," Cardiovascular Research, 8, pp. 647-655 (1974).
Zucker, et al., "Chronic Baroreceptor Activation Enhances Survival in Dogs with Pacing-Induced Heart Failure," Journal of the American Heart Association, Hypertension (2007).
PCT Application No. PCT/US2015/020116, Search Report and Written Opinion dated Jul. 6, 2015, 12 pages.

\* cited by examiner

IMPLANTABLE NEUROSTIMULATOR-IMPLEMENTED METHOD FOR MANAGING BRADYCARDIA THROUGH VAGUS NERVE STIMULATION

CROSS REFERENCE TO RELATED APPLICATIONS

This application is a continuation of U.S. patent application Ser. No. 13/554,656, filed Jul. 20, 2012 the disclosure of which is incorporated by reference herein in its entirety.

FIELD

This application relates in general to chronic cardiac dysfunction therapy and, in particular, to an implantable neurostimulator-implemented method for managing bradycardia through vagus nerve stimulation.

BACKGROUND

Congestive heart failure (CHF) is a progressive and physically debilitating chronic condition in which the heart is unable to supply sufficient blood flow to meet the body's needs. Pathologically, CHF is characterized by an elevated neuroexitatory state accompanied by impaired arterial and cardiopulmonary baroreflex function and reduced vagal activity. CHF is initiated by cardiac dysfunction, which triggers compensatory activations of the sympathoadrenal (sympathetic) nervous and the renin-angiotensin-aldosterone hormonal systems. Initially, these mechanisms help the heart compensate for deteriorating pumping function, yet over time, overdriven sympathetic activation and increased heart rate promote progressive left ventricular dysfunction and deleterious remodeling.

Sympathetic nervous system activation also significantly increases the risk and severity of bradycardia. Parasympathetic activity generally dominates over sympathetic activity. Consequently, increases in parasympathetic activity due to the triggering of CHF compensatory mechanisms can evoke pronounced bradycardia in light of the already high level of sympathetic activity stemming from chronic cardiac dysfunction. Pathologic bradycardia are categorized as either atrial, atrioventricular or ventricular, based upon the level of disturbance to normal impulse generation and conduction. Sick sinus bradycardia, a form of atrial bradycardia, is caused by sinus node malfunction. Atrioventricular nodal bradycardia occurs due to an absence of electrical impulse from the sinus node. Ventricular bradycardia occurs as the result of atrioventricular block due to an impairment in impulse conduction.

Chronic cardiac dysfunction stems from an autonomic imbalance of the sympathetic and parasympathetic nervous systems that, if left untreated, leads to cardiac arrhythmogenesis, including bradycardia, progressively worsening cardiac function and eventual death. The current standard of care for managing chronic cardiac dysfunction mandates prescription of pharmacological agents, including diuretics, angiotensin-converting enzyme inhibitors, angiotensin receptor blockers, beta-blockers, and aldosterone antagonists, and dietary and lifestyle changes. However, the effectiveness of these measures is only palliative, not curative, and patients often suffer side effects and comorbidities due to disease progression, such as pulmonary edema, sleep apnea, and myocardial ischemia.

Cardiac resynchronization therapy (CRT) has recently become available to those chronic cardiac dysfunction patients with impaired systolic function. CRT restores synchronous heartbeat through coordinated bi-ventricular pacing that helps improve contractile cardiac performance. However, CRT only addresses systolic dysfunction and is limited to patients exhibiting a wide QRS complex (mechanical dyssynchrony) and reduced left ventricular ejection fraction.

Neural stimulation has been proposed as a complementary treatment for chronic cardiac dysfunction that directly addresses the underlying autonomic nervous system imbalance, rather than relieving symptoms or directly pacing heart muscle. Activity within and among elements of both sympathetic and parasympathetic nervous systems regulate cardiovascular function by exerting high resolution control over key biological processes mediated by ionic currents flowing across cell membranes. Cumulatively, in a healthy person, the autonomic regulation of these biological processes results in stable homeostasis of heart rate and normal contractile performance. However, when disease processes derange autonomic function, homeostasis is lost and cardiovascular function is degraded; contractile performance thus becomes suboptimal and heart rate modulation is distorted in ways that create a positive feedback loop that promotes progression of chronic cardiac dysfunction and ultimately risks CHF. Neural stimulation can break the positive feedback loop through the suppression of excessive neural activation by electrically modulating select vagus nerve fibers. The electrical modulation may help improve cardiac mechanical function and reduce the heart's intrinsic nervous system's propensity to induce atrial and ventricular arrhythmias, including bradycardia, during chronic autonomic nervous system imbalance.

Notwithstanding, vagus nerve stimulation (VNS) is currently only approved for the clinical treatment of drug-refractory epilepsy and depression, although VNS has been proposed as a long-term therapeutic treatment of CHF. Conventional therapeutic alteration of cardiac vagal efferent activation through electrical stimulation targets only the efferent nerves of the parasympathetic nervous system and is clinically insufficient to restore autonomic balance. Any therapeutic effect on parasympathetic activation clinically occurs as a result of incidental recruitment of afferent parasympathetic nerve fibers and not as an intended and desired outcome of the efferent-centric neurostimulation, such as described in Sabbah et al., "Vagus Nerve Stimulation in Experimental Heart Failure," Heart Fail. Rev., 16:171-178 (2011), the disclosure of which is incorporated by reference. The Sabbah paper discusses canine studies using a vagus stimulation device, manufactured by BioControl Medical Ltd., Yehud, Israel, which includes a signal generator, right ventricular endocardial sensing lead, and right vagus nerve cuff stimulation lead. The sensing leads enable stimulation of the right vagus nerve to be synchronized to the cardiac cycle through closed-loop heart rate control. A bipolar nerve cuff electrode is surgically implanted on the right vagus nerve at the mid-cervical position. An asymmetric bi-polar multi-contact cuff electrode provides cathodic induction of action potentials while simultaneously applying asymmetric anodal blocks that lead to preferential, but not exclusive, activation of vagal efferent fibers. Electrical stimulation of the right cervical vagus nerve is delivered only when heart rate increases beyond a preset threshold. Stimulation is provided at an impulse rate and intensity intended to reduce basal heart rate by ten percent by preferential stimulation of efferent vagus nerve fibers leading to the heart while blocking afferent neural impulses to the brain. Although effective in restoring baroreflex sensitivity and, in the canine model, increasing left ventricular ejection fraction and decreasing left ventricular end diastolic and end systolic volumes, restoration of autonomic balance was not addressed.

Other uses of electrical nerve stimulation for therapeutic treatment of various physiological conditions are described. For instance, U.S. Pat. No. 6,600,954, issued Jul. 29, 2003 to Cohen et al. discloses a method and apparatus for selective control of nerve fibers. An electrode device is applied to a nerve bundle capable of generating, upon activation, unidirectional action potentials to be propagated through both small diameter and large diameter sensory fibers in the nerve bundle, and away from the central nervous system. The device is particularly useful for reducing pain sensations in the legs and arms.

U.S. Pat. No. 6,684,105, issued Jan. 27, 2004 to Cohen et al. discloses an apparatus for treatment of disorders by unidirectional nerve stimulation. An apparatus for treating a specific condition includes a set of one or more electrode devices that are applied to selected sites of the central or peripheral nervous system of the patient. For some applications, a signal is applied to a nerve, such as the vagus nerve, to stimulate efferent fibers and treat motility disorders, or to a portion of the vagus nerve innervating the stomach to produce a sensation of satiety or hunger. For other applications, a signal is applied to the vagus nerve to modulate electrical activity in the brain and rouse a comatose patient, or to treat epilepsy and involuntary movement disorders.

U.S. Pat. No. 7,123,961, issued Oct. 17, 2006 to Kroll et al. discloses stimulation of autonomic nerves. An autonomic nerve is stimulated to affect cardiac function using a stimulation device in electrical communication with the heart by way of three leads suitable for delivering multi-chamber stimulation and shock therapy. In addition, the device includes a fourth lead having three electrodes positioned in or near the heart, or near an autonomic nerve remote from the heart. Power is delivered to the electrodes at a set power level. The power is delivered at a reduced level if cardiac function was affected.

U.S. Pat. No. 7,225,017, issued May 29, 2007 to Shelchuk discloses terminating ventricular tachycardia in connection with any stimulation device that is configured or configurable to stimulate nerves, or stimulate and shock a patient's heart. Parasympathetic stimulation is used to augment anti-tachycardia pacing, cardioversion, or defibrillation therapy. To sense atrial or ventricular cardiac signals and provide chamber pacing therapy, particularly on the left side of the patient's heart, the stimulation device is coupled to a lead designed for placement in the coronary sinus or its tributary veins. Cardioversion stimulation is delivered to a parasympathetic pathway upon detecting a ventricular tachycardia. A stimulation pulse is delivered via the lead to one or more electrodes positioned proximate to the parasympathetic pathway according to stimulation pulse parameters based at least in part on the probability of reinitiation of an arrhythmia. In a further embodiment, the stimulation pulse is delivered post inspiration or during a refractory period to cause a release of acetylcholine. The stimulation device can further include a "rate-responsive" physiologic sensor to adjust pacing stimulation rate according to the exercise state of the patient or in response to changes in cardiac output.

U.S. Pat. No. 7,277,761, issued Oct. 2, 2007 to Shelchuk discloses vagal stimulation for improving cardiac function in heart failure or CHF patients. An autonomic nerve is stimulated to affect cardiac function using a stimulation device in electrical communication with the heart by way of three leads suitable for delivering multi-chamber endocardial stimulation and shock therapy. In addition, the device includes a fourth lead having three electrodes positioned in or near the heart, or near an autonomic nerve remote from the heart. A need for increased cardiac output is detected through the lead and a stimulation pulse is delivered proximate to the left vagosympathetic trunk or branch to thereby stimulate a parasympathetic nerve. If the stimulation has caused sufficient increase in cardiac output, ventricular pacing may then be initiated at an appropriately reduced rate.

U.S. Pat. No. 7,295,881, issued Nov. 13, 2007 to Cohen et al. discloses nerve branch-specific action potential activation, inhibition and monitoring. Two preferably unidirectional electrode configurations flank a nerve junction from which a preselected nerve branch issues, proximally and distally to the junction, with respect to the brain. Selective nerve branch stimulation can be used in conjunction with nerve-branch specific stimulation to achieve selective stimulation of a specific range of fiber diameters, substantially restricted to a preselected nerve branch, including heart rate control, where activating only the vagal B nerve fibers in the heart, and not vagal A nerve fibers that innervate other muscles, can be desirous.

U.S. Pat. No. 7,778,703, issued Aug. 17, 2010 to Gross et al. discloses selective nerve fiber stimulation for treating heart conditions. An electrode device is adapted to be coupled to a vagus nerve of a subject and a control unit drives the electrode device by applying stimulating and inhibiting currents to the vagus nerve, which are capable of respectively inducing action potentials in a therapeutic direction in a first set and a second set of nerve fibers in the vagus nerve and inhibiting action potentials in the therapeutic direction in the second set of nerve fibers only. The nerve fibers in the second set have larger diameters than the nerve fibers in the first set. The control unit typically drives the electrode device to apply signals to the vagus nerve to induce the propagation of efferent action potentials towards the heart and suppress artificially-induced afferent action potentials toward the brain. Patient control is not mentioned.

U.S. Pat. No. 7,813,805, issued Oct. 12, 2010 to Farazi and U.S. Pat. No. 7,869,869, issued Jan. 11, 2011 to Farazi both disclose subcardiac threshold vagus nerve stimulation. A vagus nerve stimulator is configured to generate electrical pulses below a cardiac threshold, which are transmitted to a vagus nerve, so as to inhibit or reduce injury resulting from ischemia. The cardiac threshold is a threshold for energy delivered to the heart above which there is a slowing of the heart rate or conduction velocity. In operation, the vagus nerve stimulator generates the electrical pulses below the cardiac threshold, such that heart rate is not affected. Patient control is also not mentioned.

Finally, U.S. Pat. No. 7,885,709, issued Feb. 8, 2011 to Ben-David discloses nerve stimulation for treating disorders. A control unit drives an electrode device to stimulate the vagus nerve, so as to modify heart rate variability, or to reduce heart rate, by suppressing the adrenergic (sympathetic) system. The vagus stimulation reduces the release of catecholamines in the heart, thus lowering adrenergic tone at its source. For some applications, the control unit synchronizes the stimulation with the cardiac cycle, while for other applications, the stimulation can be applied, for example, in a series of pulses. To reduce heart rate, stimulation is applied using a target heart rate lower than the subject's normal average heart rate. In one embodiment, the control unit is further adapted to detect bradycardia and to terminate heart rate regulation immediately upon such detection, such as by ceasing vagus stimulation of the sympathetic nervous system. Additionally, the control unit can use an algorithm that reacts to regulate heart rate when the heart rate crosses limits that are predefined, for instance, a low limit of 40 bpm and a high limit of 140 bpm, or as determined in real time, such as responsive to sensed physiological values.

Accordingly, a need remains for an approach to therapeutically treating chronic cardiac dysfunction, including CHF, and cardiac arrhythmogenesis, specifically bradycardia, through a form of VNS to restore autonomic balance.

SUMMARY

Excessive sustained activation of the sympathetic nervous system has a deleterious effect on long term cardiac performance and increases the risk of bradycardia and related forms of arrhythmia. Bi-directional afferent and efferent neural stimulation through the vagus nerve can beneficially restore autonomic balance and improve long term patient outcome. The neural stimulation is provided in a low level maintenance dose independent of cardiac cycle. VNS delivery can be provided through an implantable vagus neurostimulator and electrode lead, which suspends delivery of the maintenance dose upon sensing a condition indicative of bradycardia. VNS delivery is only continually resumed if, during post-suspension monitoring, bradycardia is not found to recur as a result of VNS resumption.

One embodiment provides an implantable neurostimulator and implantable neurostimulator-implemented method for managing bradycardia through vagus nerve stimulation. An operating mode of the implantable neurostimulator is stored, which includes parametrically defining a maintenance dose of the electrical therapeutic stimulation tuned to restore cardiac autonomic balance through continuously-cycling, intermittent and periodic electrical pulses. The maintenance dose is therapeutically delivered to the vagus nerve via a pulse generator included in the neurostimulator through a pair of helical electrodes via an electrically coupled nerve stimulation therapy lead independent of cardiac cycle. The patient's physiology is monitored via a physiological sensor included in the implantable neurostimulator, and upon sensing a condition indicative of bradycardia, the delivery of the maintenance dose by the pulse generator to the vagus nerve is suspended. A progressively increasing amount of time is spent waiting via a controller included in the implantable neurostimulator and, upon sensing a condition indicative of an absence or termination of the bradycardia, a progressively increasing partial maintenance dose is delivered to the vagus nerve via the pulse generator.

A further embodiment provides an implantable neurostimulator and implantable neurostimulator-implemented method for managing bradycardia through vagus nerve stimulation. A maintenance dose of electrical therapeutic stimulation for delivery via an implantable neurostimulator is defined and tuned to restore cardiac autonomic balance through continuously-cycling, intermittent and periodic electrical pulses. The maintenance dose is delivered to the vagus nerve through a pair of helical electrodes via a stimulation therapy lead electrically coupled nerve to a pulse generator included in the implantable neurostimulator. The maintenance dose is therapeutically delivered via the pulse generator to the vagus nerve in both afferent and efferent directions of a cervical vagus nerve of a patient independent of cardiac cycle. The patient's physiology is periodically monitored via a physiological sensor included in the implantable neurostimulator. Upon sensing a condition indicative of bradycardia, the delivery of the maintenance dose to the vagus nerve is suspended. A back-off delay including an amount of time that increases over each previous back-off delay is determined via a controller included in the implantable neurostimulator. Upon expiry of the back-off delay, the patient's physiology is checked via the physiological sensor. Upon sensing a condition indicative of an absence or termination of the bradycardia, the maintenance dose is delivered at a partial duty cycle to the vagus nerve via the pulse generator. The monitoring of the patient's physiology is resumed via the physiological sensor. Upon sensing a condition indicative of a continued absence of bradycardia, the duty cycle of the maintenance dose is gradually increased.

By restoring autonomic balance, therapeutic VNS operates acutely to decrease heart rate, increase heart rate variability and coronary flow, reduce cardiac workload through vasodilation, and improve left ventricular relaxation without aggravating comorbid bradycardia or other cardiac arrhythmic conditions. Over the long term, low dosage VNS provides the chronic benefits of decreased negative cytokine production, increased baroreflex sensitivity, increased respiratory gas exchange efficiency, favorable gene expression, renin-angiotensin-aldosterone system down-regulation, and anti-arrhythmic, anti-apoptotic, and ectopy-reducing anti-inflammatory effects.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Functional behavior of heart tissue is influenced by the autonomic nervous system, which plays a key pathogenic role in the cause of and the biological response to cardiovascular disease. Complex changes in autonomic control of the cardiovascular systems of patients suffering from a cardiovascular disease push the autonomic nervous system out of balance and favor increased sympathetic and decreased parasympathetic central outflow. The imbalance is accompanied by pronounced bradycardia due to the elevated parasympathetic activity triggered to respond to the compensatory sympathetic activity. Peripheral neurostimulation therapies that target the imbalance of the autonomic nervous system found in individuals with severe CHF have been shown to improve outcomes. Specifically, propagating efferent and afferent action potentials through bi-directional autonomic regulation therapy activates both parasympathetic afferent and efferent nerve fibers in the vagus nerve simultaneously. The therapy directly restores autonomic balance by engaging both medullary and cardiac reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart, while afferent action potentials influence central elements of the nervous system.

Figure 1:
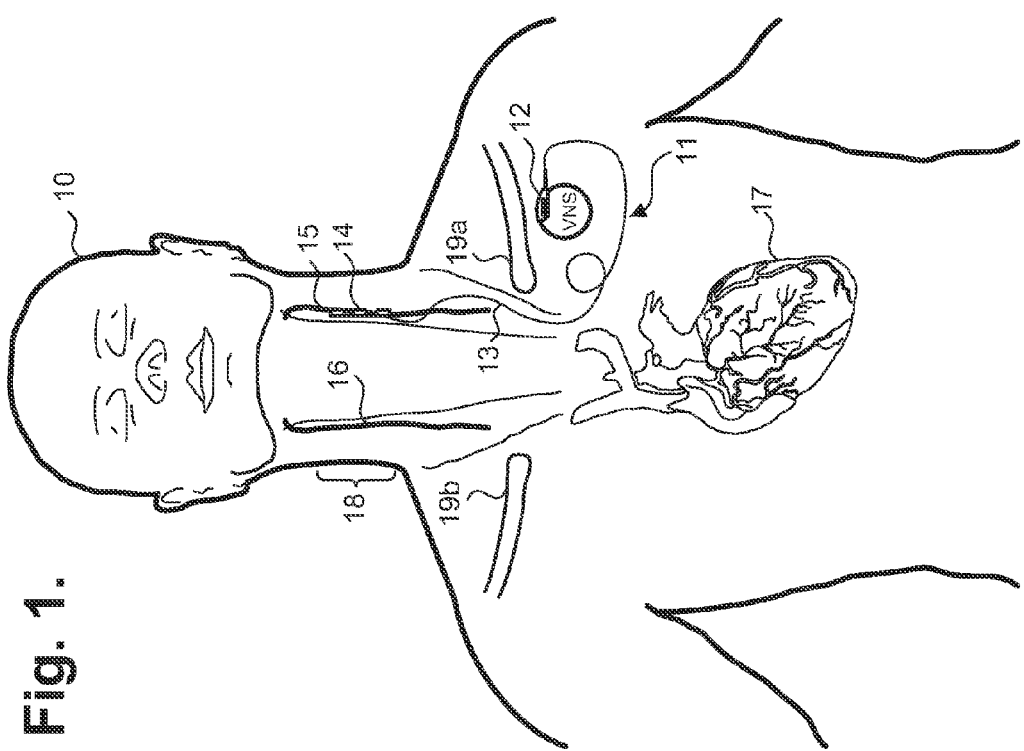
FIG. 1 is a front anatomical diagram showing, by way of example, placement of an implantable vagus stimulation device in a male patient, in accordance with one embodiment.

An implantable vagus nerve stimulator, such as used to treat drug-refractory epilepsy and depression, can be adapted for use in managing chronic cardiac dysfunction through therapeutic bi-directional vagal stimulation. FIG. 1 is a front anatomical diagram showing, by way of example, placement of an implantable vagus stimulation device 11 in a male patient 10, in accordance with one embodiment. The VNS provided through the stimulation device 11 operates under several mechanisms of action. These mechanisms include increasing parasympathetic outflow and inhibiting sympathetic effects by blocking norepinephrine release. More importantly, VNS triggers the release of acetylcholine (ACh) into the synaptic cleft, which has beneficial anti-arrhythmic, anti-apoptotic, and ectopy-reducing anti-inflammatory effects.

The implantable vagus stimulation device 11 includes at least three implanted components, an implantable neurostimulator 12, a therapy lead 13, and helical electrodes 14. The implantable vagus stimulation device 11 can be remotely accessed following implant through an external programmer by which the neurostimulator 12 can be remotely checked and programmed by healthcare professionals; an external magnet, such as described in commonly-assigned U.S. Patent application, entitled "Implantable Device For Facilitating Control Of Electrical Stimulation Of Cervical Vagus Nerves For Treatment Of Chronic Cardiac Dysfunction," Ser. No. 13/314,130, filed on Dec. 7, 2011, pending, the disclosure of which is incorporated by reference, for basic patient control; and an electromagnetic controller, such as described in commonly-assigned U.S. Patent application, entitled "Vagus Nerve Neurostimulator With Multiple Patient-Selectable Modes For Treating Chronic Cardiac Dysfunction," Ser. No. 13/352,244, filed on Jan. 17, 2012, pending, the disclosure of which is incorporated by reference, that enables the patient 10 to exercise increased control over therapy delivery and suspension. Together, the implantable vagus stimulation device 11 and one or more of the external components form a VNS therapeutic delivery system.

The neurostimulator 12 is implanted in the patient's right or left pectoral region generally on the same side (ipsilateral) of the patient's body as the vagus nerve 15, 16 to be stimulated, although other neurostimulator-vagus nerve configurations, including contra-lateral and bi-lateral are possible. The helical electrodes 14 are generally implanted on the vagus nerve 15, 16 about halfway between the clavicle 19a-b and the mastoid process. The therapy lead 13 and helical electrodes 14 are implanted by first exposing the carotid sheath and chosen vagus nerve 15, 16 through a latero-cervical incision on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the therapy lead 13 is guided to the neurostimulator 12 and securely connected.

The stimulation device 11 bi-directionally stimulates the vagus nerve 15, 16 through application of continuously-cycling, intermittent and periodic electrical stimuli, which are parametrically defined through stored stimulation parameters and timing cycles. In one embodiment, the autonomic regulation therapy is provided in a low level maintenance dose independent of cardiac cycle to activate both parasympathetic afferent and efferent nerve fibers in the vagus nerve simultaneously. Both sympathetic and parasympathetic nerve fibers are stimulated through the helical electrodes 14 of the stimulation device 11. Stimulation of the cervical vagus nerve results in propagation of action potentials in both afferent and efferent directions from the site of stimulation to restore autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation device 11, although stimulation of the right vagus nerve 16 has a moderately stronger affect on heart rate (on the order of approximately 20% stronger) than left vagus nerve 15 stimulation at the same parametric levels.

Figure 2A:
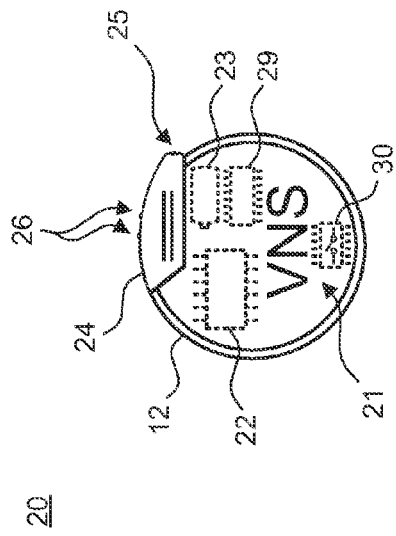
FIGS. 2A and 2B are diagrams respectively showing the implantable neurostimulator and the simulation therapy lead of FIG. 1.
Figure 2B:
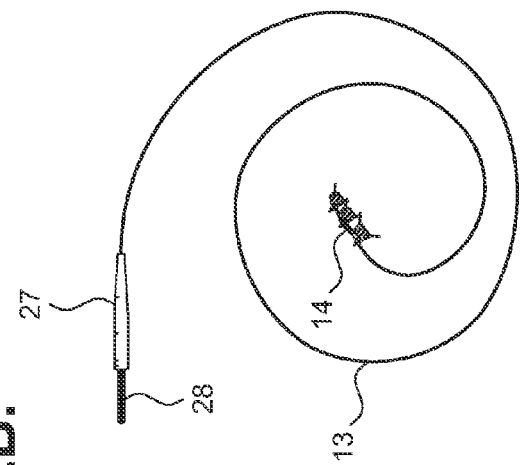

The VNS therapy is autonomously delivered to the patient's vagus nerve 15, 16 through three implanted components that include a neurostimulator 12, therapy lead 13, and helical electrodes 14. FIGS. 2A and 2B are diagrams respectively showing the implantable neurostimulator 12 and the simulation therapy lead 13 of FIG. 1. In one embodiment, the neurostimulator 12 can be adapted from a VNS Therapy AspireHC Model 105 pulse generator or a VNS Therapy AspireSR Model 106 pulse generator, both manufactured and sold by Cyberonics, Inc., Houston, Tex., although other manufactures and types of single-pin receptacle implantable VNS neurostimulators could also be used. The stimulation therapy lead 13 and helical electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based on helical electrode inner diameter, although other manufactures and types of single-pin receptacle-compatible therapy leads and electrodes could also be used.

Referring first to FIG. 2A, the neurostimulator 12 provides continuously-cycling, intermittent and periodic ON-OFF cycles of vagal stimulation in a maintenance does that when, applied to the vagus nerve through the electrodes 14, produce action potentials in the underlying nerves that propagate bi-directionally. Afferently propagating action potentials activate the medial medullary sites responsible for central reflex control and efferently propagating action potentials activate both the heart's intrinsic nervous system and the heart directly. The neurostimulator 12 includes an electrical pulse generator that is tuned to restore autonomic balance by triggering action potentials that propagate both afferently and efferently within the vagus nerve 15, 16. The neurostimulator 12 is enclosed in a hermetically sealed housing 21 constructed of a biocompatible, implantation-safe material, such as titanium. The housing 21 contains electronic circuitry 22 powered by a primary battery 22, such as a lithium carbon monoflouride battery. The electronic circuitry 22 is implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, and collects and stores telemetry information; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and persistent (static) forms of memory, such as firmware within which the stimulation parameters and timing cycles can be stored. Other electronic circuitry and components, such as an integrated heart rate sensor, are possible.

Externally, the neurostimulator 12 includes a header 24 to securely receive and connect to the therapy lead 13. In one embodiment, the header 24 encloses a receptacle 25 into which a single pin for the therapy lead 13 can be received, although two or more receptacles could also be provided, along with the requisite additional electronic circuitry 22. The header 24 internally includes a lead connector block (not shown) and a set of set screws 26.

The neurostimulator 12 is preferably interrogated prior to implantation and throughout the therapeutic period with a healthcare provider-operable external programmer and programming wand (not shown) for checking proper operation, downloading recorded data, diagnosing problems, and programming operational parameters. Generally, use of the external programmer is restricted to healthcare providers, while more limited manual control is provided to the patient through "magnet mode." In one embodiment, the external programmer executes application software specially designed to interrogate the neurostimulator 12. The programming computer interfaces to the programming wand through a standardized wired or wireless data connection. The programming wand can be adapted from a Model 201 Programming Wand, manufactured and sold by Cyberonics, Inc. and the application software can be adapted from the Model 250 Programming Software suite, licensed by Cyberonics, Inc. Other configurations and combinations of external programmer, programming wand and application software are possible.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12, such as described in commonly-assigned U.S. Patent application, entitled "Computer-Implemented System and Method for Selecting Therapy Profiles of Electrical Stimulation of Cervical Vagus Nerves for Treatment of Chronic Cardiac Dysfunction," Ser. No. 13/314,138, filed on Dec. 7, 2011, pending, the disclosure of which is incorporated by reference.

Referring next to FIG. 2B, the therapy lead 13 delivers an electrical signal from the neurostimulator 12 to the vagus nerve 15, 16 via the helical electrodes 14. On a proximal end, the therapy lead 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the therapy lead 13 to the neurostimulator 12. On a distal end, the therapy lead 13 terminates with the helical electrode 14, which bifurcates into a pair of anodic and cathodic electrodes 62 (as further described below with reference to FIG. 4). In one embodiment, the lead connector 27 is manufactured using silicone and the connector pin 28 is made of stainless steel, although other suitable materials could be used, as well. The insulated lead body 13 utilizes a silicone-insulated alloy conductor material.

Preferably, the helical electrodes 14 are placed over the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned over the patient's vagus nerve oriented with the end of the helical electrodes 14 facing the patient's head. At the distal end, the insulated electrical lead body 13 is bifurcated into a pair of lead bodies that are connected to a pair of electrodes proper. The polarity of the electrodes could be configured into a monopolar cathode, a proximal anode and a distal cathode, or a proximal cathode and a distal anode.

Therapeutically, the VNS is delivered as a cardiac cycle-independent maintenance dose through continuously-cycling, intermittent and periodic cycles of electrical pulses and rest (inhibition), which are system output behaviors that are pre-specified within the neurostimulator 12 through the stored stimulation parameters and timing cycles implemented in firmware and executed by the microprocessor. The neurostimulator 12 can operate either with or without an integrated heart rate sensor, such as respectively described in commonly-assigned U.S. Patent application, entitled "Implantable Device for Providing Electrical Stimulation of Cervical Vagus Nerves for Treatment of Chronic Cardiac Dysfunction with Leadless Heart Rate Monitoring," Ser. No. 13/314,126, filed on Dec. 7, 2011, pending, and U.S. Patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are hereby incorporated by reference herein in their entirety. Additionally, where an integrated leadless heart rate monitor is available, the neurostimulator 12 can provide autonomic cardiovascular drive evaluation and self-controlled titration, such as respectively described in commonly-assigned U.S. Patent application, entitled "Implantable Device for Evaluating Autonomic Cardiovascular Drive in a Patient Suffering from Chronic Cardiac Dysfunction," Ser. No. 13/314,133, filed on Dec. 7, 2011, pending, and U.S. Patent application, entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, pending, the disclosures of which are hereby incorporated by reference herein in their entirety.

Figure 3:
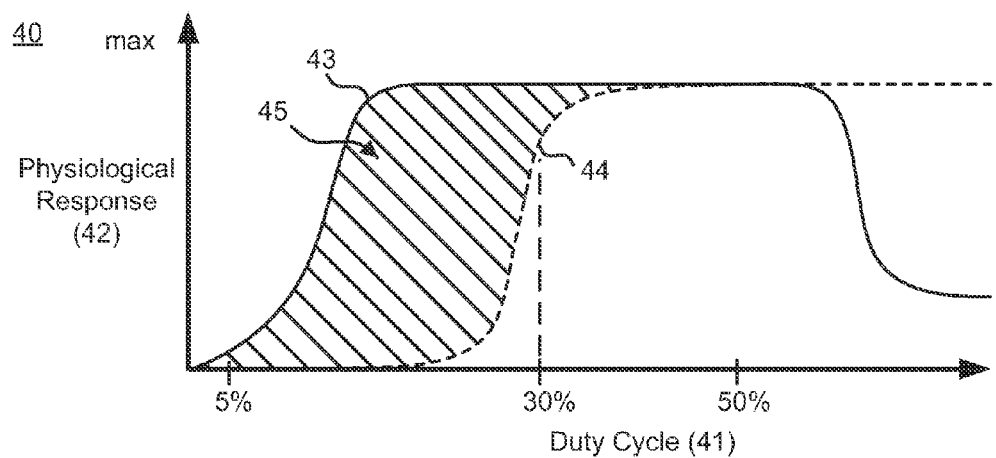
FIG. 3 is a graph showing, by way of example, the relationship between the targeted therapeutic efficacy and the extent of potential side effects resulting from use of the implantable neurostimulator of FIG. 1.

VNS is delivered as a heart failure therapy independent of cardiac cycle and in a maintenance dose low enough to not elicit side-effects, such as cardiac arrhythmias. The VNS can be delivered with a periodic duty cycle in the range of 2% to 89% with a preferred range of around 4% to 36% that is delivered as a low intensity maintenance dose. The selection of duty cycle is a tradeoff between competing medical considerations. FIG. 3 is a graph 40 showing, by way of example, the relationship between the targeted therapeutic efficacy 43 and the extent of potential side effects 44 resulting from use of the implantable neurostimulator 12 of FIG. 1. The x-axis represents the duty cycle 41. The duty cycle is determined by dividing the stimulation time by the sum of the ON and OFF times of the neurostimulator 12. However, the stimulation time may also need to include ramp-up time and ramp-down time, where the stimulation frequency exceeds a minimum threshold (as further described below with reference to FIG. 5). The y-axis represents physiological response 42 to VNS therapy. The physiological response 42 can be expressed quantitatively for a given duty cycle 41 as a function of the targeted therapeutic efficacy 43 and the extent of potential side effects 44, as described infra. The maximum level of physiological response 42 ("max") signifies the highest point of targeted therapeutic efficacy 43 or potential side effects 44.

Targeted therapeutic efficacy 43 and the extent of potential side effects 44 can be expressed as functions of duty cycle 41 and physiological response 42. The targeted therapeutic efficacy 43 represents the intended effectiveness of VNS in provoking a beneficial physiological response for a given duty cycle and can be quantified by assigning values to the various acute and chronic factors that contribute to the physiological response 42 of the patient 10 due to the delivery of therapeutic VNS. Acute factors that contribute to the targeted therapeutic efficacy 43 include increase in heart rate variability and coronary flow, reduction in cardiac workload through vasodilation, and improvement in left ventricular relaxation. Chronic factors that contribute to the targeted therapeutic efficacy 43 include decreased parasympathetic activation and increased sympathetic activation, as well as decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. These contributing factors can be combined in any manner to express the relative level of targeted therapeutic efficacy 43, including weighting particular effects more heavily than others or applying statistical or numeric functions based directly on or derived from observed physiological changes. Empirically, targeted therapeutic efficacy 43 steeply increases beginning at around a 5% duty cycle, and levels off in a plateau near the maximum level of physiological response at around a 30% duty cycle. Thereafter, targeted therapeutic efficacy 43 begins decreasing at around a 50% duty cycle and continues in a plateau near a 25% physiological response through the maximum 100% duty cycle.

The extent of potential side effects 44 represents the occurrence of a possible physiological effect, either adverse, such as bradycardia, or therapeutic, that is secondary to the benefit intended, which presents in the patient 10 in response to VNS and can be quantified by assigning values to the physiological effects presented due to the delivery of therapeutic VNS. The degree to which a patient 10 may be prone to exhibit side effects depends in large part upon the patient's condition, including degree of cardiac dysfunction, both acute and chronic, any comobidities, prior heart problems, family history, general health, and similar considerations. As well, the type and severity of a side effect is patient-dependent. For VNS in general, the more common surgical- and stimulation-related adverse side effects include infection, asystole, bradycardia, syncope, abnormal thinking, aspiration pneumonia, device site reaction, acute renal failure, nerve paralysis, hypesthesia, facial paresis, vocal cord paralysis, facial paralysis, hemidiaphragm paralysis, recurrent laryngeal injury, urinary retention, and low grade fever. The more common non-adverse side effects include hoarseness, voice alteration, increased coughing, pharyngitis, paresthesia, dyspnea, dyspepsia, nausea, and laryngismus. Less common side effects, including adverse events, include ataxia, hypesthesia, increase coughing, insomnia, muscle movement or twitching associated with stimulation, nausea, pain, paresthesia, pharyngitis, vomiting, aspiration, blood clotting, choking sensation, nerve damage, vasculature damage, device migration or extrusion, dizziness, dysphagia, duodenal or gastric ulcer, ear pain, face flushing, facial paralysis or paresis, implant rejection, fibrous tissue formation, fluid pocket formation, hiccupping, incision site pain, irritability, laryngeal irritation, hemidiaphragm paralysis, vocal cord paralysis, muscle pain, neck pain, painful or irregular stimulation, seroma, skin or tissue reaction, stomach discomfort, tinnitus, tooth pain, unusual scarring at incision site, vagus nerve paralysis, weight change, worsening of asthma or bronchitis. These quantified physiological effects can be combined in any manner to express the relative level of extent of potential side effects 44, including weighting particular effects more heavily than others or applying statistical or numeric functions based directly on or derived from observed physiological changes. Empirically, the extent of potential side effects 44 is initially low until around a 25% duty cycle, at which point the potential begins to steeply increase. The extent of potential side effects 44 levels off in a plateau near the maximum level of physiological response at around a 50% duty cycle through the maximum 100% duty cycle.

Figure 4:
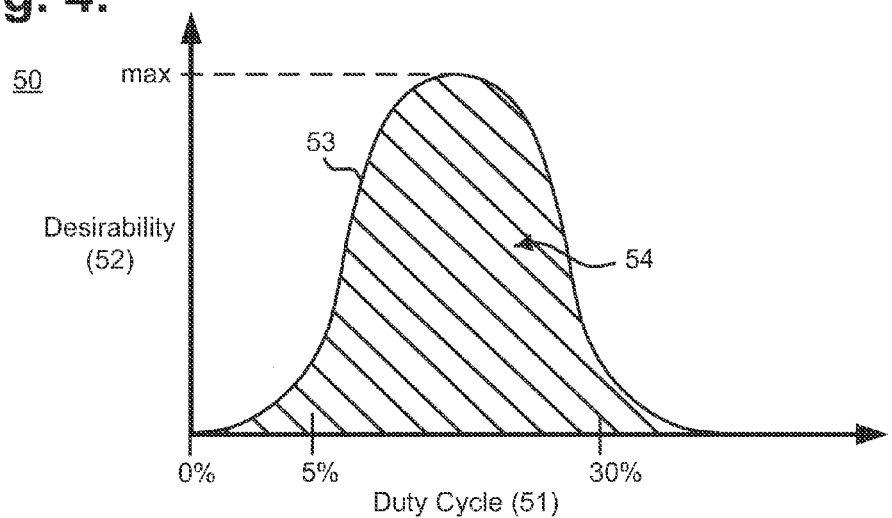
FIG. 4 is a graph showing, by way of example, the optimal duty cycle range based on the intersection depicted in FIG. 3.

The intersection 45 of the targeted therapeutic efficacy 43 and the extent of potential side effects 44 represents one optimal duty cycle range for VNS. FIG. 4 is a graph 50 showing, by way of example, the optimal duty cycle range 53 based on the intersection 45 depicted in FIG. 3. The x-axis represents the duty cycle 51 as a percentage of stimulation time over inhibition time. The y-axis represents the desirability 52 of operating the neurostimulator 12 at a given duty cycle 51. The optimal duty range 53 is a function 54 of the intersection 44 of the targeted therapeutic efficacy 43 and the extent of potential side effects 44. The desirability 52 can be expressed quantitatively for a given duty cycle 51 as a function of the values of the targeted therapeutic efficacy 43 and the extent of potential side effects 44 at their point of intersection in the graph 40 of FIG. 3. The maximum level of desirability 52 ("max") signifies a tradeoff that occurs at the point of highest targeted therapeutic efficacy 43 in light of lowest potential side effects 44 and that point will typically be found within the range of a 5% to 30% duty cycle 51. Other expressions of duty cycles and related factors are possible.

Figure 5:
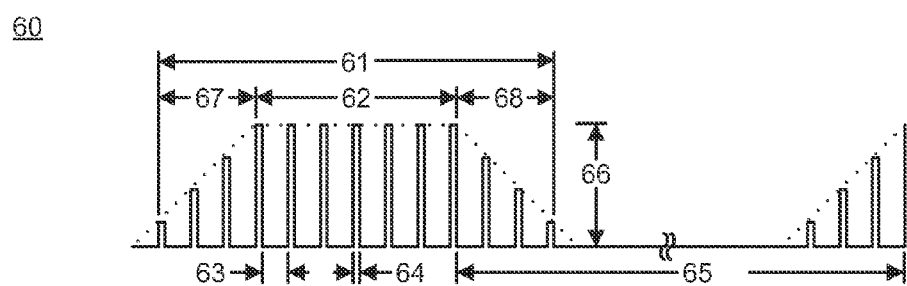
FIG. 5 is a timing diagram showing, by way of example, a stimulation cycle and an inhibition cycle of VNS as provided by implantable neurostimulator of FIG. 1.

VNS is delivered in a low level maintenance dose that uses alternating cycles of stimuli application (ON) and stimuli inhibition (OFF) that are tuned to both efferently activate the heart's intrinsic nervous system and heart tissue and afferently activate the patient's central reflexes. FIG. 5 is a timing diagram showing, by way of example, a stimulation cycle and an inhibition cycle of VNS 60 as provided by implantable neurostimulator 12 of FIG. 1. The stimulation parameters enable the electrical stimulation pulse output by the neurostimulator 12 to be varied by both amplitude (output current 66) and duration (pulse width 64). The number of output pulses delivered per second determines the signal frequency 63. In one embodiment, a pulse width in the range of 100 to 250 μsec delivers between 0.02 and 50 mA of output current at a signal frequency of about 20 Hz, although other therapeutic values could be used as appropriate.

In the simplest case, the stimulation time is the time period during which the neurostimulator 12 is ON and delivering pulses of stimulation. The OFF time 65 is always the time period occurring in-between stimulation times 61 during which the neurostimulator 12 is OFF and inhibited from delivering stimulation. In one embodiment, the neurostimulator 12 implements a ramp-up time 67 and a ramp-down time 68 that respectively precede and follow the ON time 62 during which the neurostimulator 12 is ON and delivering pulses of stimulation at the full output current 66. The ramp-up time 67 and ramp-down time 68 are used when the stimulation frequency is at least 10 Hz, although other minimum thresholds could be used, and both times last two seconds, although other time periods could also be used. The ramp-up time 67 and ramp-down time 68 allow the strength of the output current 66 of each output pulse to be gradually increased and decreased, thereby avoiding unnecessary trauma to the vagus nerve due to sudden delivery or inhibition of stimulation at full strength.

Figure 6:
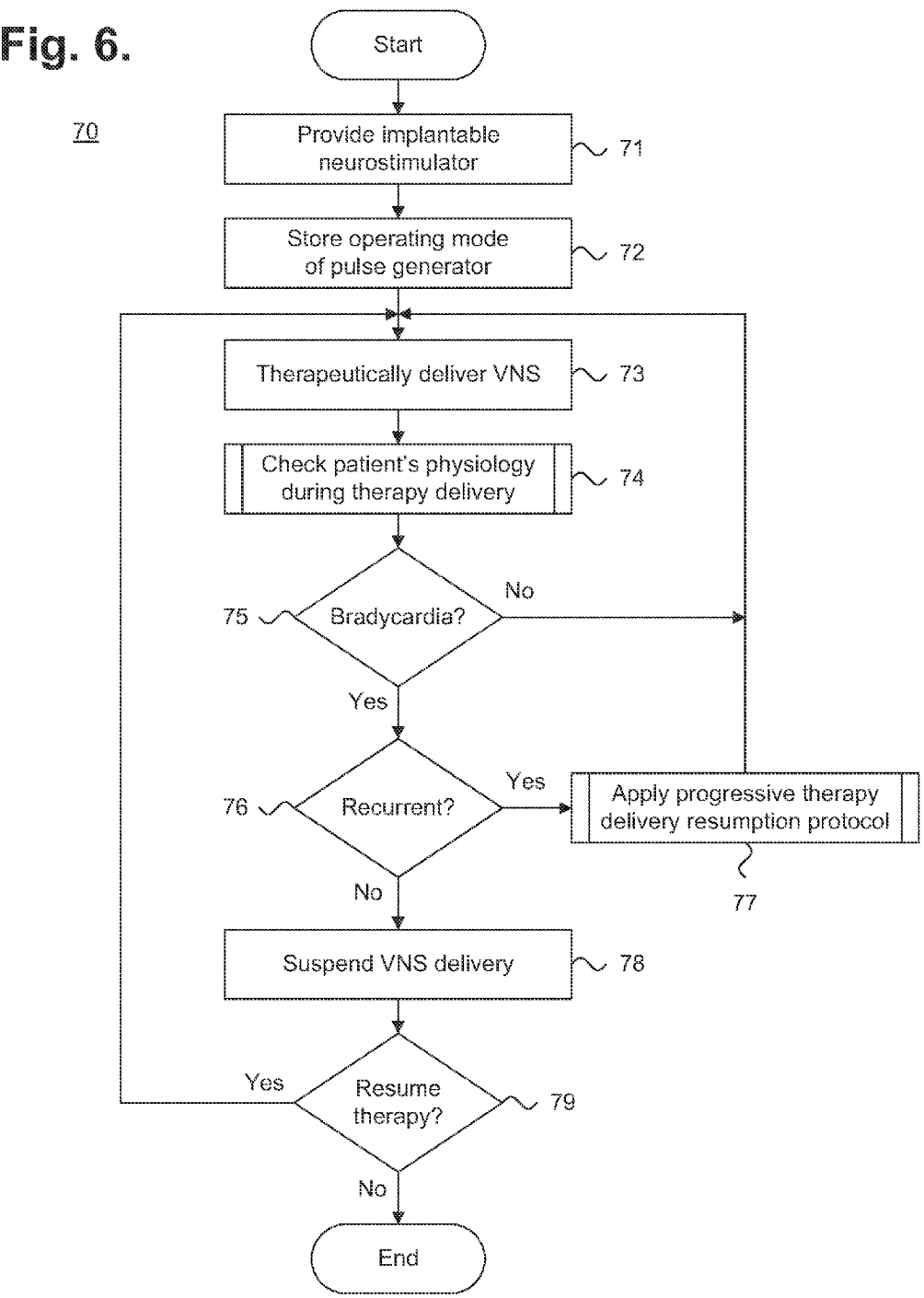
FIG. 6 is a flow diagram showing an implantable neurostimulator-implemented method for managing bradycardia through vagus nerve stimulation, in accordance with one embodiment.

Therapeutic VNS can potentially exacerbate pathological bradycardia. The increased parasympathetic activity that occurs in response to the triggering of CHF compensatory mechanisms increases the risk of bradycardia. VNS therapy can be suspended upon the occurrence of bradycardia, after which therapy only resumes if bradycardia does not recur. FIG. 6 is a flow diagram showing an implantable neurostimulator-implemented method for managing bradycardia through vagus nerve stimulation 70, in accordance with one embodiment. The method is implemented on the stimulation device 11, the operation of which is parametrically defined through stored stimulation parameters and timing cycles.

Preliminarily, an implantable neurostimulator 12, which includes a pulse generator 11, a nerve stimulation therapy lead 13, and a pair of helical electrodes 14, is provided (step 71). In an alternative embodiment, electrodes may be implanted with no implanted neurostimulator or leads. Power may be provided to the electrodes from an external power source and neurostimulator through wireless RF or inductive coupling. Such an embodiment may result in less surgical time and trauma to the patient. Referring back to FIG. 6, the pulse generator 11 delivers electrical therapeutic stimulation to the cervical vagus nerve of a patient 10 in both afferent and efferent directions on either the left or right vagus nerve 15, 16. The pulse generator stores an operating mode (step 72) that parametrically defines a low level maintenance dose of the stimulation, which is tuned, as described supra, to restore cardiac autonomic balance through continuously-cycling, intermittent and periodic electrical pulses.

Therapeutic VNS is delivered to the vagus nerve independent of cardiac cycle (step 73). During therapy delivery, the patient's physiology is checked for bradycardia (step 74), as further described below with reference to FIGS. 7 and 8. If a monitored condition of the patient is indicative of bradycardia, that is, the patient's physiology indicates the onset or presence of bradycardia (step 75), the delivery of the maintenance dose is suspended. In the context of therapeutic VNS delivery, however, bradycardia that presents recurrently following the resumption of therapy (step 76) is suspended and provisionally resumed by applying a progressive therapy delivery resumption protocol (step 77), which incrementally increases duty cycle and delay, as further described below with reference to FIG. 9. Otherwise, if bradycardia presents independently of a recent resumption of therapy delivery and is therefore not recurrent (step 76), VNS delivery is temporarily suspended (step 78), after which time therapy delivery resumes (step 79). The period of suspension will be between 15 and 30 minutes, or as appropriate to the situation. In one embodiment, the duration of suspension may be determined based on continued monitoring of the patient's heart rate or sinus rhythm, including the type of bradycardia or arrhythmia detected.

The onset or presence of pathological bradycardia can be determined by heart rate or normal sinus rhythm through an endocardial electrogram. Other physiological measures are possible. For instance, sick sinus bradycardia, a form of atrial bradycardia, presents with a resting heart rate below 60 bpm, while atrioventricular nodal bradycardia presents with a normal QRS complex accompanied by an inverted P wave. Conversely, ventricular bradycardia presents with a wide QRS complex and heart rate between 20 and 40 bpm, while junctional ventricular bradycardia presents with a narrow QRS complex and heart rate between 40 and 60 bpm. Once suspended, VNS delivery is only continually resumed if, during post-suspension monitoring, bradycardia is not found to recur as a result of VNS resumption (step 77), the delivery of the maintenance dose is resumed (step 73). Otherwise, therapy remains suspended.

Figure 7:
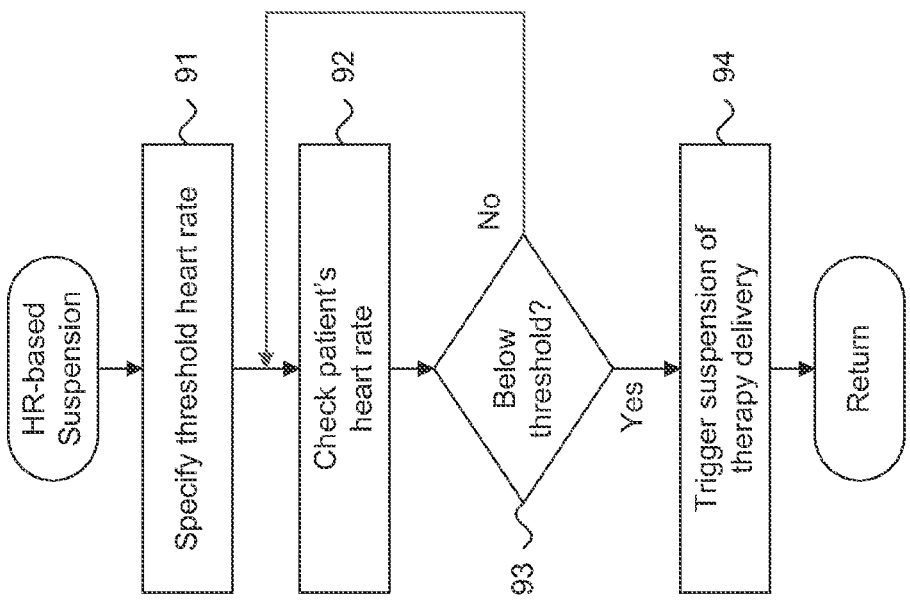
FIG. 7 is a flow diagram showing a routine for suspending therapy delivery based on normal sinus rhythm for use with the method of FIG. 6.

The onset or presence of bradycardia can be identified by evaluating sinus rhythm or heart rate through a physiological sensor. FIG. 7 is a flow diagram showing a routine for suspending therapy delivery based on normal sinus rhythm 80 for use with the method 70 of FIG. 6. Normal sinus rhythm is a state of normal heart rate and rhythm. Parameters that define normal sinus rhythm are specified (step 81), which can be parametrically programmed into the implantable neurostimulator 12. During VNS therapy delivery, the patent's heart rate is monitored (step 82) using, for instance, a single block electrode on the vagus nerve and the neurostimulator's header 24, which respectively form a sinus rhythm sensor. In a further embodiment, the neurostimulator 12 could be augmented with an endocardial sensing electrode. If the sinus rhythm is not normal (step 83), for example, the P wave is inverted or the QRS complex is too wide or narrow, bradycardia has onset or exists and therapy delivery is suspended (step 84).

Figure 8:
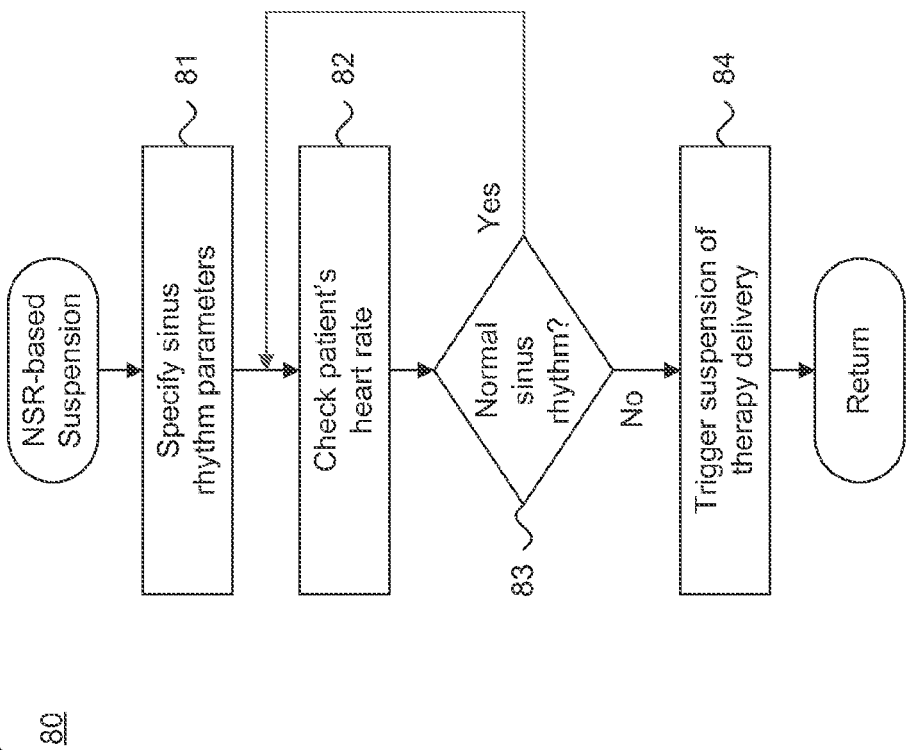
FIG. 8 is a flow diagram showing an alternative routine for suspending therapy delivery based on heart rate for use with the method of FIG. 6, in accordance with a further embodiment.

Alternatively, heart rate can be monitored to sense bradycardia. FIG. 8 is a flow diagram showing an alternative (or additional) routine for suspending therapy delivery based on heart rate 90 for use with the method 70 of FIG. 6, in accordance with a further embodiment. The implantable neurostimulator 12 includes a leadless heart rate sensor, such as available with a VNS Therapy AspireSR Model 106 pulse generator, manufactured and sold by Cyberonics, Inc., Houston, Tex. A minimum acceptable threshold heart rate, such as 50 bpm, is specified (step 91). During VNS therapy delivery, the patient's heart rate is checked (step 92). If the heart rate falls below the threshold (step 93), bradycardia has onset or exists and therapy delivery is suspended (step 94).

Figure 9:
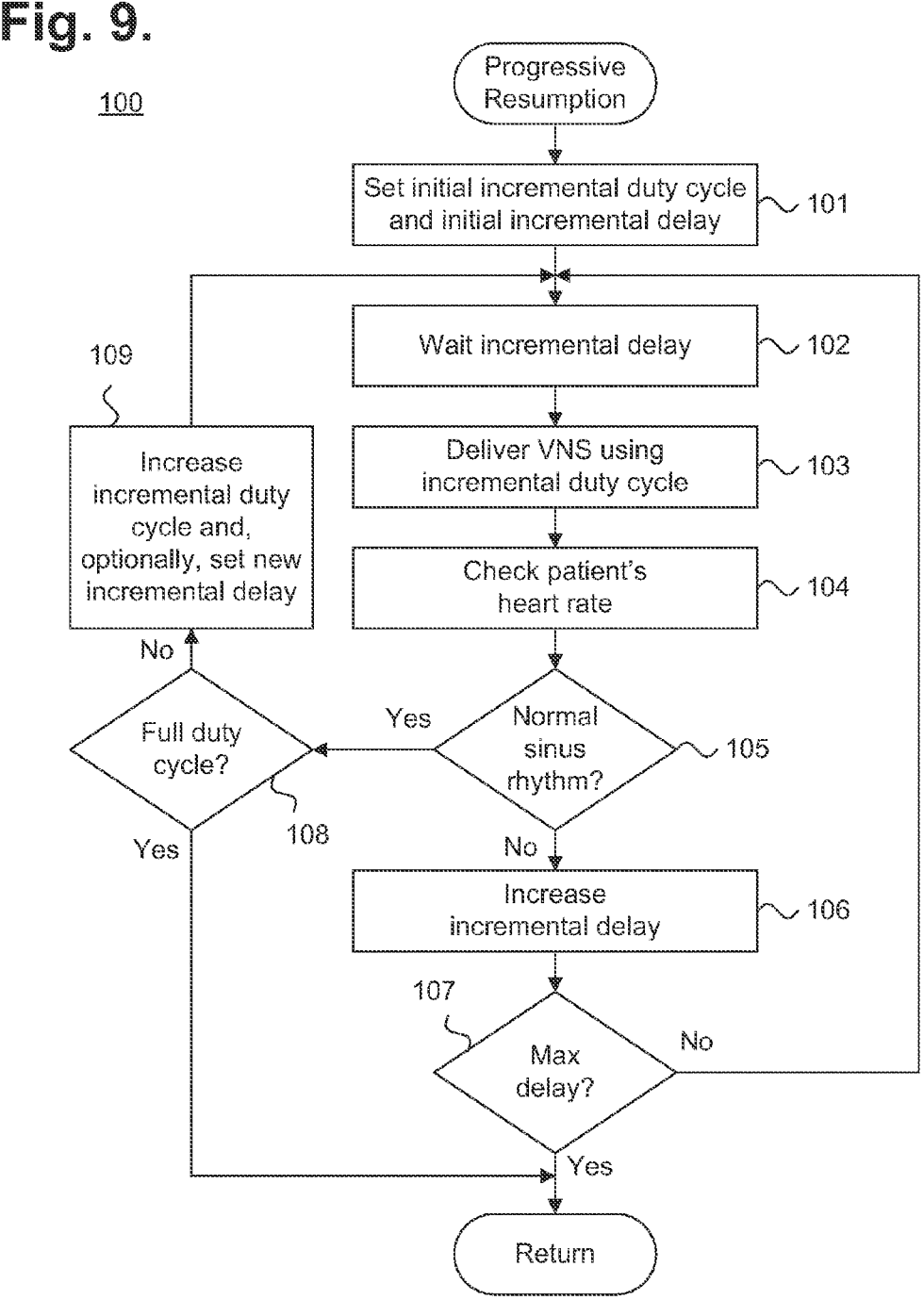
FIG. 9 is a flow diagram showing a routine for progressively resuming therapy delivery for use with the method of FIG. 6.

Following the resumption of therapy, VNS will not be continually resumed at the normal full duty cycle if bradycardia recurs to counter the chance that the VNS is either aggravating or causing the bradycardia. A progressive therapy delivery resumption protocol is instead used to gradually resume VNS therapy delivery. FIG. 9 is a flow diagram showing a routine for progressively resuming therapy delivery 100 for use with the method 70 of FIG. 6. The protocol progressively adapts to the recurrence of bradycardia in the patient 11. Temporally, the protocol uses an exponential back-off delay to increase the amount of time lapsing between attempts at resuming VNS therapy. Therapeutically, the protocol steadily increases the duty cycle of VNS delivery once bradycardia appears to no longer be recurring.

Initially, an initial incremental partial duty cycle and initial incremental delay are set (step 101), which can be parametrically programmed into the implantable neurostimulator 12. In one embodiment, the initial incremental duty cycle begins with a two-second pulse train and an initial incremental delay of ten minutes, although other initial incremental duty cycles and delays could be used. VNS therapy is suspended for the period of the initial incremental delay (step 102), after which VNS stimulation is delivered at the initial incremental duty cycle (step 103). Monitoring of the patient's physiology is resumed and the patient's heart rate is periodically checked (step 104) using, for instance, a block electrode on the vagus nerve or an endocardial sensing electrode and, if the patient's condition remains clear of indications of bradycardia, the incremental duty cycle is gradually increased with each successive heart rate check until the full maintenance duty cycle is reached.

The amount of time needed before bradycardia terminates varies and does not generally follow a temporally linear, and therefore predictable, curve from onset to termination. As well, regularly monitoring the patient's physiology throughout the period of therapy suspension can needlessly consume pulse generator 11 resources, while resuming VNS therapy after a fixed period of delay can expose the patient to potentially harmful VNS too soon. Consequently, the pulse generator 11 applies a form of exponential back-off delay algorithm between attempts at resuming VNS delivery. If, after the initial incremental period of delay, the sinus rhythm is still abnormal (step 105), the pulse generator 11 increases the duration of the incremental delay (step 106).

Figure 10:
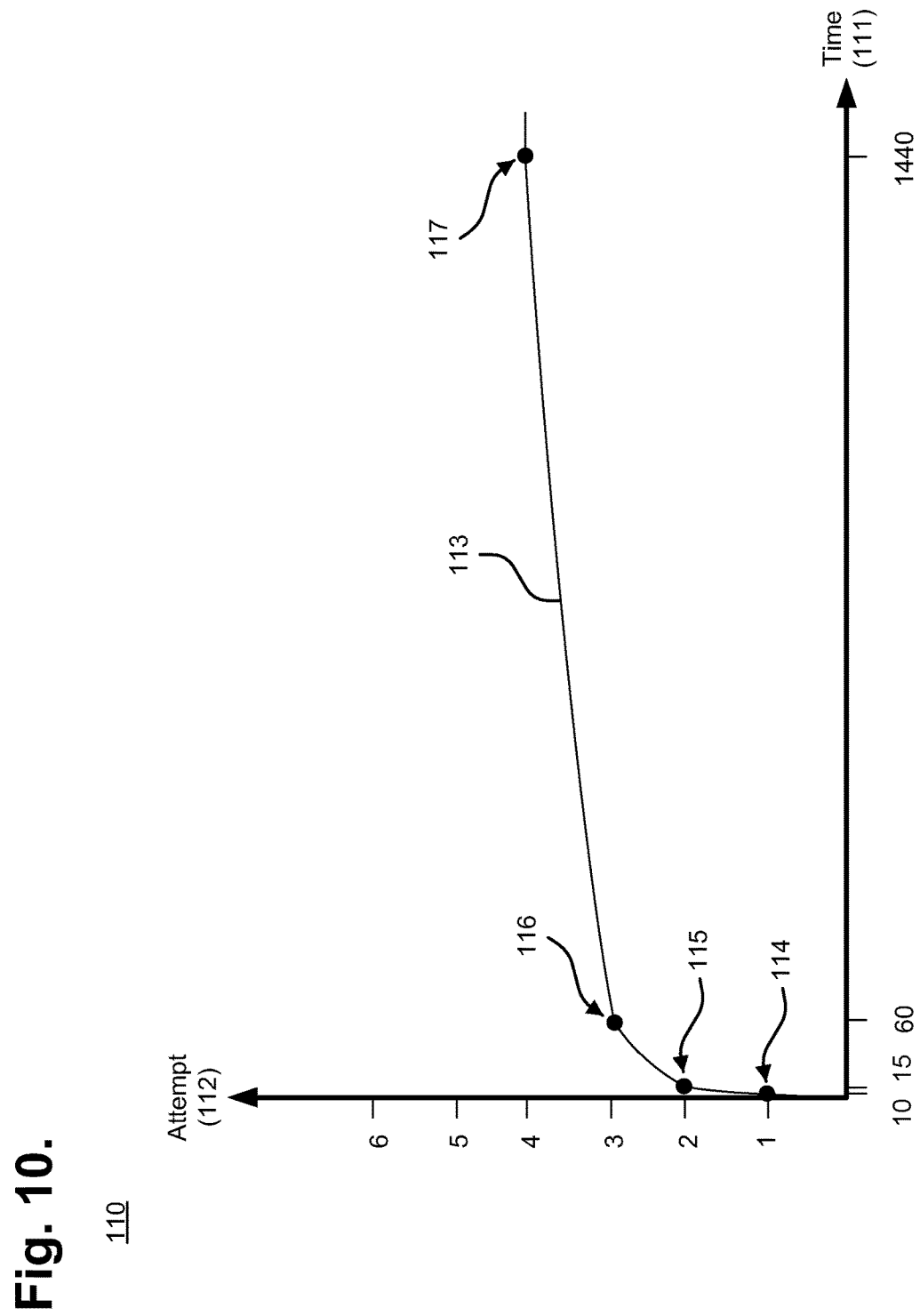
FIG. 10 is a timing diagram showing, by way of example, an exponential back-off delay as used in the routine of FIG. 9.

The incremental waiting period generated by the exponential back-off delay algorithm can be parametrically adjusted. FIG. 10 is a timing diagram 110 showing, by way of example, an exponential back-off delay 113 as used in the routine 100 of FIG. 9. The x-axis 111 represents time in minutes, although other time increments could be used. The y-axis 112 represents the number of attempts at resuming therapy delivery, that is, the number of times that the patient's physiology is checked. Here, the pulse generator 11 waits an initial incremental delay of 10 minutes (point 114) before delivering VNS at the initial incremental duty cycle and checking the patient's physiology for the first time, followed by increasingly larger delays of 15 minutes (point 115), one hour (point 116), 24 hours (point 117), and three days (not shown), assuming continuing bradycardia, before suspending VNS therapy indefinitely once the maximum delay has been reached. Other forms of incrementally increasing the delay could be used, including binary exponential, truncated binary exponential and stochastic back-off algorithms.

Referring back to FIG. 9, VNS therapy is again suspended for the period of the increased incremental delay (step 102), after which VNS stimulation is delivered (step 103) and the patient's heart rate checked (step 104). The cycle of increasing the incremental delay, delivering VNS and checking the patient's heart rate (steps 102-107) is repeated, until either normal sinus rhythm is restored (step 105) or the maximum delay has been reached (step 107), after which VNS therapy is suspended indefinitely.

Once normal sinus rhythm has successfully been restored (step 105), the duty cycle is then also incrementally increased (step 109) until the full duty cycle has been reached (step 108). Optionally, a new period of incremental delay can also be set (step 109). VNS therapy is again suspended for the period of the incremental delay (step 102), after which VNS stimulation is delivered at the incrementally increased duty cycle (step 103) and the patient's heart rate checked (step 104). The cycle of increasing the incremental duty cycle, delivering VNS and checking the patient's heart rate (steps 102-105, 108 and 109) is repeated, until the full duty cycle has been reached (step 108) or abnormal sinus rhythm that indicates a recurrence of bradycardia is encountered (step 105), after which VNS therapy is suspended once more using the next period of incremental delay at which the protocol left off.

In still further embodiments, both the suspension and resumption of therapy delivery can be titrated to gradually withdraw or introduce VNS. As well, therapy delivery can be manually suspended by providing the neurostimulator 12 with a magnetically-actuated reed switch that suspends therapy delivery in response to a remotely applied magnetic signal.

While the invention has been particularly shown and described as referenced to the embodiments thereof, those skilled in the art will understand that the foregoing and other changes in form and detail may be made therein without departing from the spirit and scope.

What is claimed is:

1. A method for managing bradycardia through vagus nerve stimulation, comprising the steps of:
  defining a maintenance dose of electrical therapeutic stimulation;
  delivering the maintenance dose to a vagus nerve of a patient independent of cardiac cycle;
  periodically monitoring the patient's physiology via a physiological sensor;
  upon sensing a condition indicative of bradycardia, suspending the delivery of the maintenance dose to the vagus nerve, comprising:

determining a back-off delay comprising an amount of time that increases over each previous back-off delay;

upon expiry of the back-off delay, checking the patient's physiology via the physiological sensor; and upon sensing a condition indicative of an absence or termination of the bradycardia, delivering the maintenance dose at a partial duty cycle to the vagus nerve;

resuming the periodic monitoring of the patient's physiology; and upon sensing a condition indicative of a continued absence of bradycardia, gradually increasing the duty cycle of the maintenance dose in response to the periodic monitoring of the patient's physiology.

2. A method according to claim 1, further comprising the steps of:

upon sensing a condition indicative of a recurrence of the bradycardia, re-suspending the delivery of the maintenance dose to the vagus nerve, comprising:

exponentially increasing the back-off delay over a back-off delay most recently used during suspension of the delivery of the maintenance dose to the vagus nerve; and upon expiry of the increasing back-off delay, checking the patient's physiology via the physiological sensor.

3. A method according to claim 2, further comprising the steps of:

continuing the re-suspension of the delivery of the maintenance dose; and terminating the delivery of the maintenance dose to the vagus nerve once a maximum back-off delay has been reached.

4. A method according to claim 1, further comprising the step of:

sensing the condition indicative of bradycardia based on at least one of abnormal sinus rhythm and heart rate falling below a minimum threshold.

5. A non-transitory computer readable storage medium storing code for executing on a computer system to perform the method according to claim 1.

6. A method according to claim 1, wherein the pulsed electrical signals propagate in both an efferent and efferent direction.

7. A method for managing bradycardia through vagus nerve stimulation, comprising the steps of:

defining a maintenance dose of electrical therapeutic stimulation, wherein the electrical therapeutic stimulation comprises a pulsed electrical signal comprising:
 a signal ON time;
 a signal OFF time;
 an output current;
 a signal frequency of approximately 10 Hz;
 a pulse width; and
 a duty cycle defined by dividing the signal ON time by the sum of the signal ON time and signal OFF time;

delivering the maintenance dose to a vagus nerve of a patient independent of cardiac cycle;

periodically monitoring the patient's physiology via a physiological sensor;

upon sensing a condition indicative of bradycardia, suspending the delivery of the maintenance dose to the vagus nerve, comprising:

determining a back-off delay comprising an amount of time that increases over each previous back-off delay;

upon expiry of the back-off delay, checking the patient's physiology via the physiological sensor; and upon sensing a condition indicative of an absence or termination of the bradycardia, delivering the maintenance dose at a partial duty cycle to the vagus nerve;

resuming the periodic monitoring of the patient's physiology; and upon sensing a condition indicative of a continued absence of bradycardia, gradually increasing the duty cycle of the maintenance dose in response to the periodic monitoring of the patient's physiology.

8. A method according to claim 7, further comprising the steps of:

upon sensing a condition indicative of a recurrence of the bradycardia, re-suspending the delivery of the maintenance dose to the vagus nerve, comprising:

exponentially increasing the back-off delay over a back-off delay most recently used during suspension of the delivery of the maintenance dose to the vagus nerve; and upon expiry of the increased back-off delay, checking the patient's physiology via the physiological sensor.

9. A method according to claim 8, further comprising the steps of:

continuing the re-suspension of the delivery of the maintenance dose; and terminating the delivery of the maintenance dose to the vagus nerve once a maximum back-off delay has been reached.

10. A method according to claim 7, further comprising the step of:

sensing the condition indicative of bradycardia based on at least one of abnormal sinus rhythm and heart rate falling below a minimum threshold.

11. A non-transitory computer readable storage medium storing code for executing on a computer system to perform the method according to claim 7.

12. A method according to claim 7, wherein the pulsed electrical signal further comprises a signal ramp-down time.

13. A method according to claim 7, wherein the pulsed electrical signal further comprises a signal ramp-up time.

14. A method according to claim 7, wherein the pulsed electrical signals propagate in both an efferent and efferent direction.

15. A method according to claim 7, wherein the duty cycle is in a range of 4% to 36%.

* * * * *